United States Patent
Witts et al.

(10) Patent No.: US 8,579,927 B2
(45) Date of Patent: Nov. 12, 2013

(54) SYSTEMS AND METHODS FOR REMOTE ENDARTERECTOMY

(75) Inventors: Jeffrey J. Witts, North Reading, MA (US); Ryan H. Connelly, Topsfield, MA (US); Michal Ursiny, Essex Junction, VT (US); Michael J. McGraw, Watertown, MA (US); James A. Yuhan, Winchester, MA (US)

(73) Assignee: LeMaitre Vascular, Inc., Burlington, MA (US)

( * ) Notice: Subject to any disclaimer, the term of this patent is extended or adjusted under 35 U.S.C. 154(b) by 12 days.

(21) Appl. No.: 13/350,377

(22) Filed: Jan. 13, 2012

(65) Prior Publication Data

US 2012/0184978 A1 Jul. 19, 2012

Related U.S. Application Data

(60) Provisional application No. 61/432,866, filed on Jan. 14, 2011.

(51) Int. Cl.
*A61B 17/22* (2006.01)

(52) U.S. Cl.
USPC .......................................................... 606/159

(58) Field of Classification Search
USPC ............ 600/36; 606/110–115, 127, 128, 159, 606/160
See application file for complete search history.

(56) References Cited

U.S. PATENT DOCUMENTS

| | | |
|---|---|---|
| 777,716 A | 12/1904 | Dennett |
| 856,927 A | 6/1907 | Straw |
| 1,167,014 A | 1/1916 | O'Brien |
| 2,944,552 A | 7/1960 | Cannon |
| 3,448,741 A | 6/1969 | Dennis et al. |
| 3,564,582 A | 2/1971 | Wai |
| 3,837,345 A | 9/1974 | Matar |
| 4,030,503 A | 6/1977 | Clark, III |

(Continued)

FOREIGN PATENT DOCUMENTS

| | | |
|---|---|---|
| EP | 0119688 | 9/1984 |
| EP | 0274846 | 7/1988 |

(Continued)

OTHER PUBLICATIONS

Ho, G., et al., "The Mollring Cutter™ Remote Endarterectomy: Preliminary Experience with a New Endovascular Technique for Treatment of Occlusive Superficial Femoral Artery Disease", Journal of Endovascular Surgery, 2(3): pp. 278-287 (1995).

(Continued)

*Primary Examiner* — Ryan Severson
(74) *Attorney, Agent, or Firm* — Greenberg Traurig, LLP; David J. Dykeman; Roman Fayerberg

(57) ABSTRACT

Systems and methods for remote endarterectomy are disclosed. In an embodiment, a device for remote endarterectomy includes an elongated member, having a proximal end, a distal end, and a longitudinal axis therebetween; an endarterectomy unit at the distal end of the elongated member formed by a first member engaged to a second member in a substantial secure alignment with the second member, wherein the endarterectomy unit has a circumferential enclosure configured to separate a plaque core from a blood vessel and an open region surrounded by the enclosure and configured to receive the separated plaque core therethrough; and an actuator coupled to the proximal end of the elongated member for translating the first member relative to the second member across the open space to transect the plaque core received in the open space.

20 Claims, 20 Drawing Sheets

(56) References Cited

U.S. PATENT DOCUMENTS

| | | |
|---|---|---|
| 4,287,890 A | 9/1981 | Fogarty |
| 4,290,427 A | 9/1981 | Chin |
| 4,315,511 A | 2/1982 | Chin |
| 4,559,927 A | 12/1985 | Chin |
| 4,574,781 A | 3/1986 | Chin |
| 4,594,996 A | 6/1986 | Ibrahim et al. |
| 4,621,636 A | 11/1986 | Fogarty |
| 4,655,217 A | 4/1987 | Reed |
| 4,665,918 A | 5/1987 | Garza et al. |
| 4,706,671 A | 11/1987 | Weinrib |
| 4,765,332 A | 8/1988 | Fischell et al. |
| 4,867,156 A | 9/1989 | Stack et al. |
| 4,887,613 A | 12/1989 | Farr et al. |
| 4,994,067 A | 2/1991 | Summers |
| 5,011,490 A | 4/1991 | Fischell et al. |
| 5,071,424 A | 12/1991 | Reger |
| 5,074,871 A | 12/1991 | Groshong |
| 5,100,423 A | 3/1992 | Fearnot |
| 5,133,360 A | 7/1992 | Spears |
| 5,133,725 A | 7/1992 | Quadri |
| 5,171,316 A | 12/1992 | Mehigan |
| 5,366,463 A | 11/1994 | Ryan |
| 5,409,454 A | 4/1995 | Fischell et al. |
| 5,480,379 A | 1/1996 | La Rosa |
| 5,820,629 A | 10/1998 | Cox |
| 5,843,102 A | 12/1998 | Kalmann et al. |
| 6,110,190 A | 8/2000 | Ginn et al. |
| 6,146,397 A | 11/2000 | Harkrider, Jr. |
| 6,193,653 B1 | 2/2001 | Evans et al. |
| 6,241,745 B1 | 6/2001 | Rosenthal |
| 6,328,749 B1 | 12/2001 | Kalmann et al. |
| 6,358,244 B1 | 3/2002 | Newman et al. |
| 6,682,542 B2 | 1/2004 | Harkrider |
| 7,163,547 B2 | 1/2007 | Majlessi |
| 7,517,352 B2 | 4/2009 | Evans et al. |
| 7,732,400 B2 | 6/2010 | Stern et al. |
| 8,133,866 B2 | 3/2012 | Stern et al. |
| 8,241,346 B2 | 8/2012 | Chobotov |

FOREIGN PATENT DOCUMENTS

| | | |
|---|---|---|
| FR | 2635962 | 3/1990 |
| GB | 2195540 | 4/1988 |
| SU | 673-273 | 7/1979 |
| SU | 1526-662 | 12/1989 |
| WO | WO 90/01969 | 3/1990 |
| WO | WO 94/04096 | 3/1994 |
| WO | WO 95/11633 | 5/1995 |

OTHER PUBLICATIONS

Joosten, H., et al., "The Mollring Cutter™ Remote Endarterectomy", Clinical Ischaemia, 6(1): pp. 14-20 (in existence as of May 30, 1996).

Remote endarterectomy using the ring strip cutter technique (in existence as of May 31, 1996).

EndoRE™ Remote Endarterectomy Devices Brochure, LeMaitre Vascular, Sep. 2008.

PCT International Search Report based on PCT/US2012/021306 dated May 11, 2012.

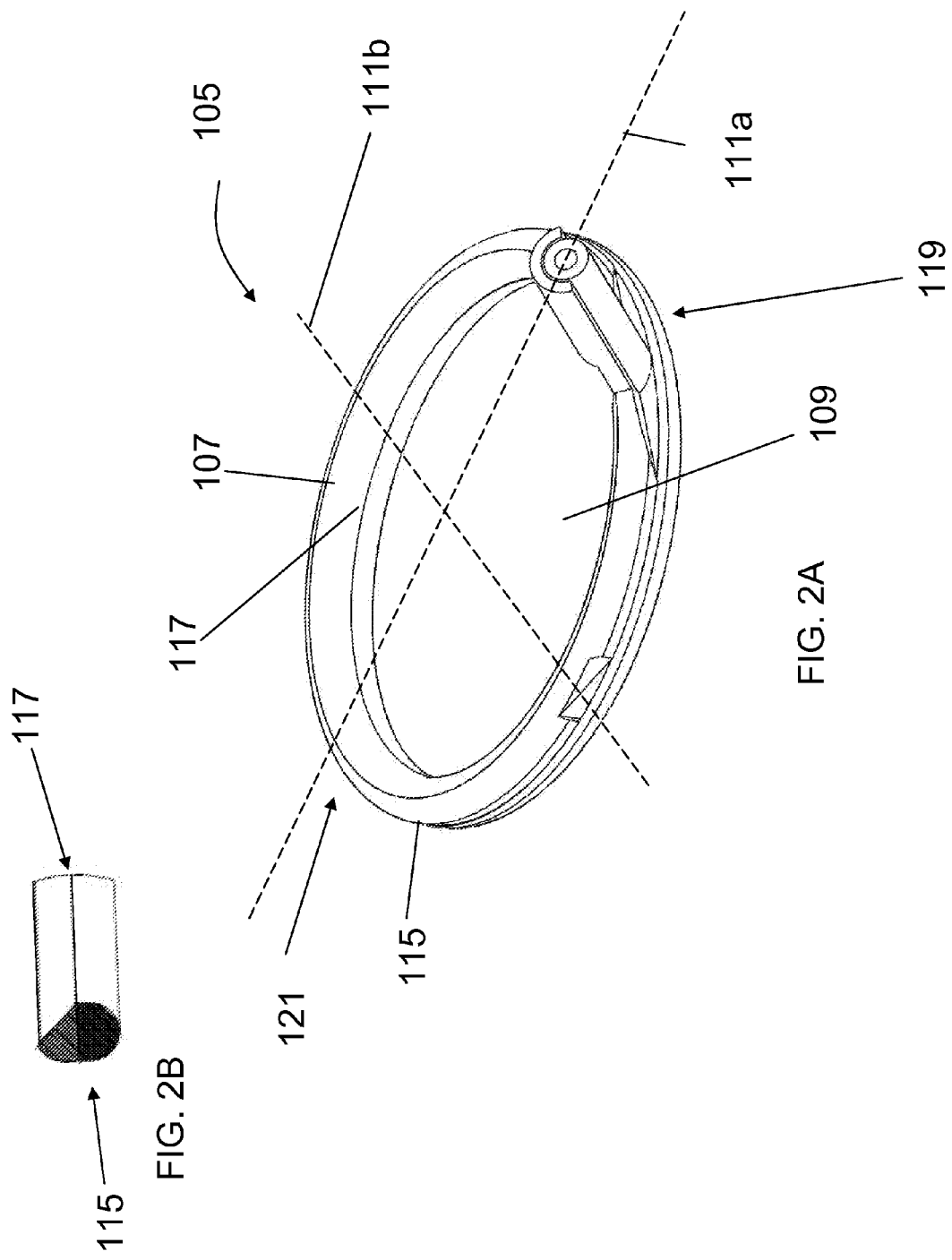

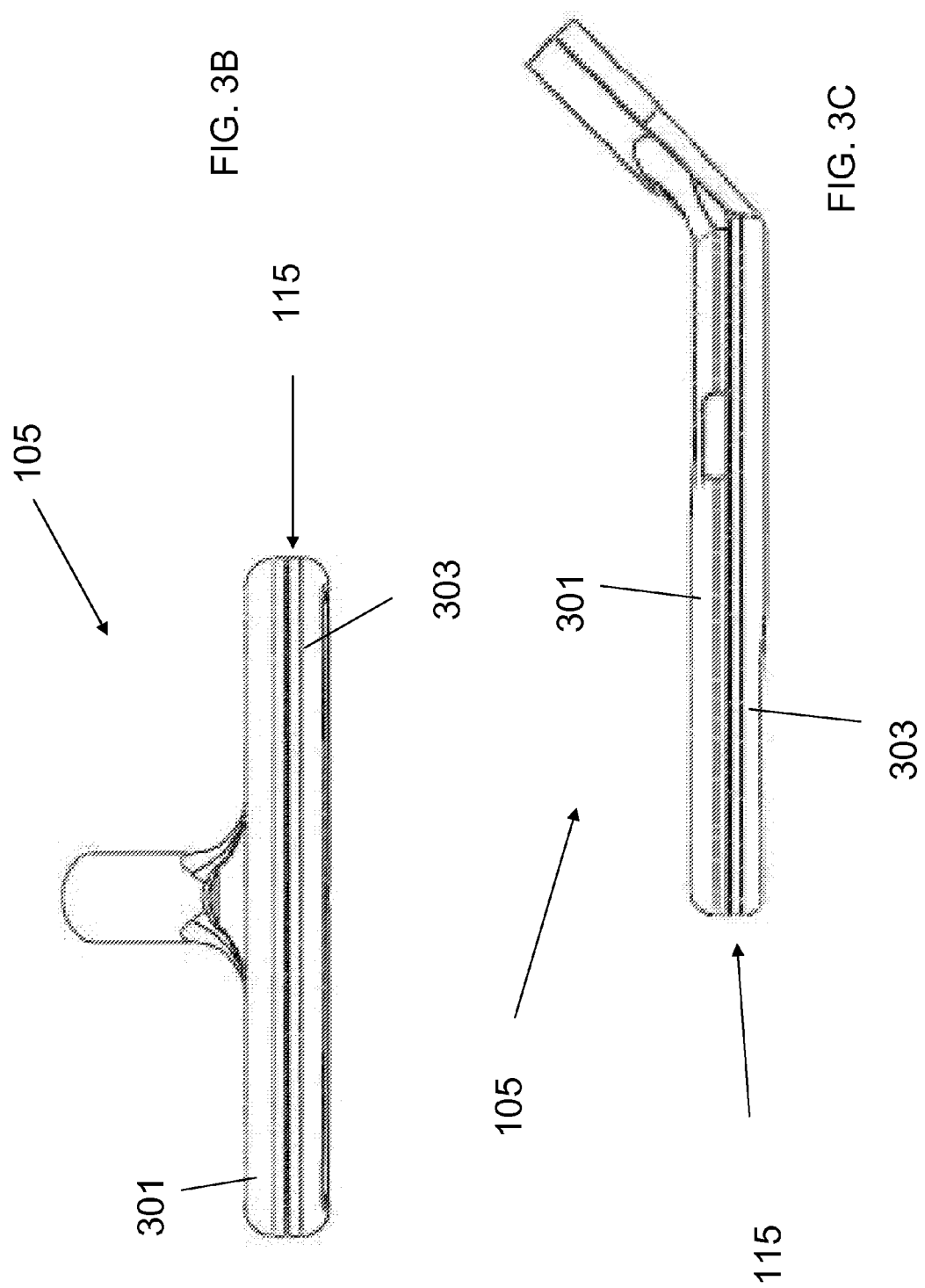

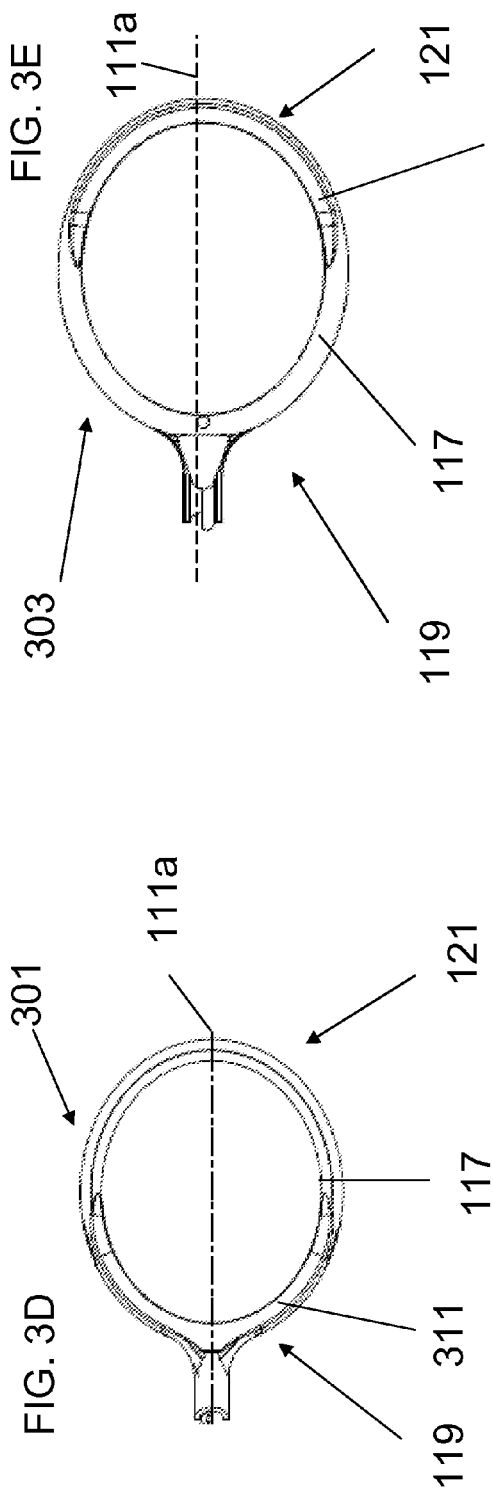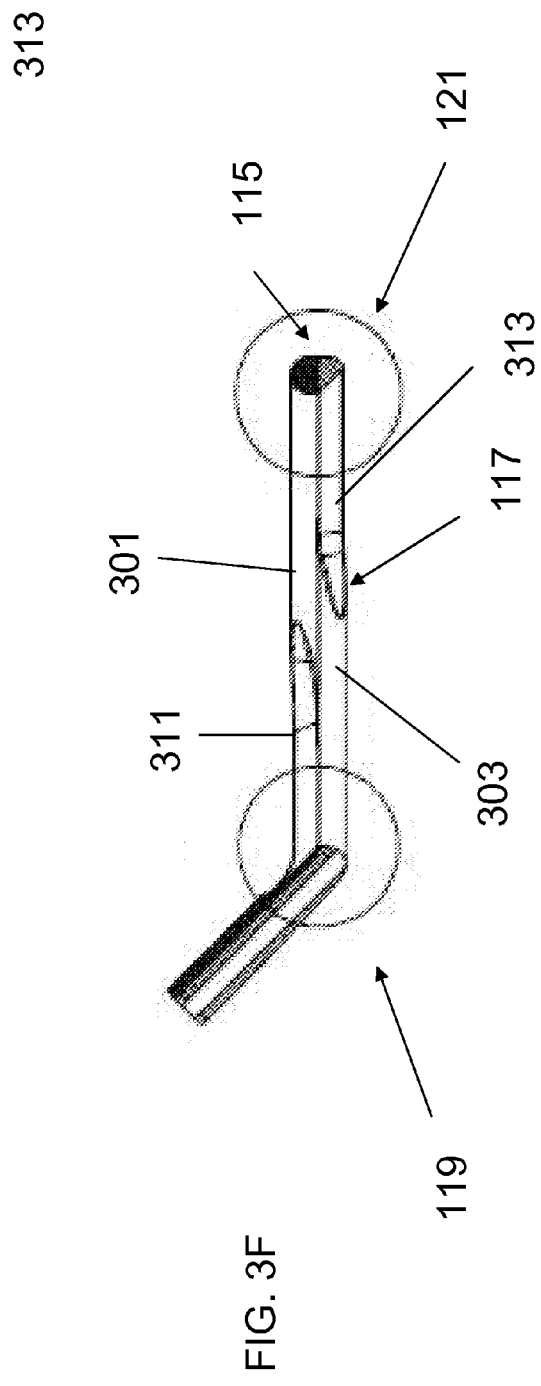

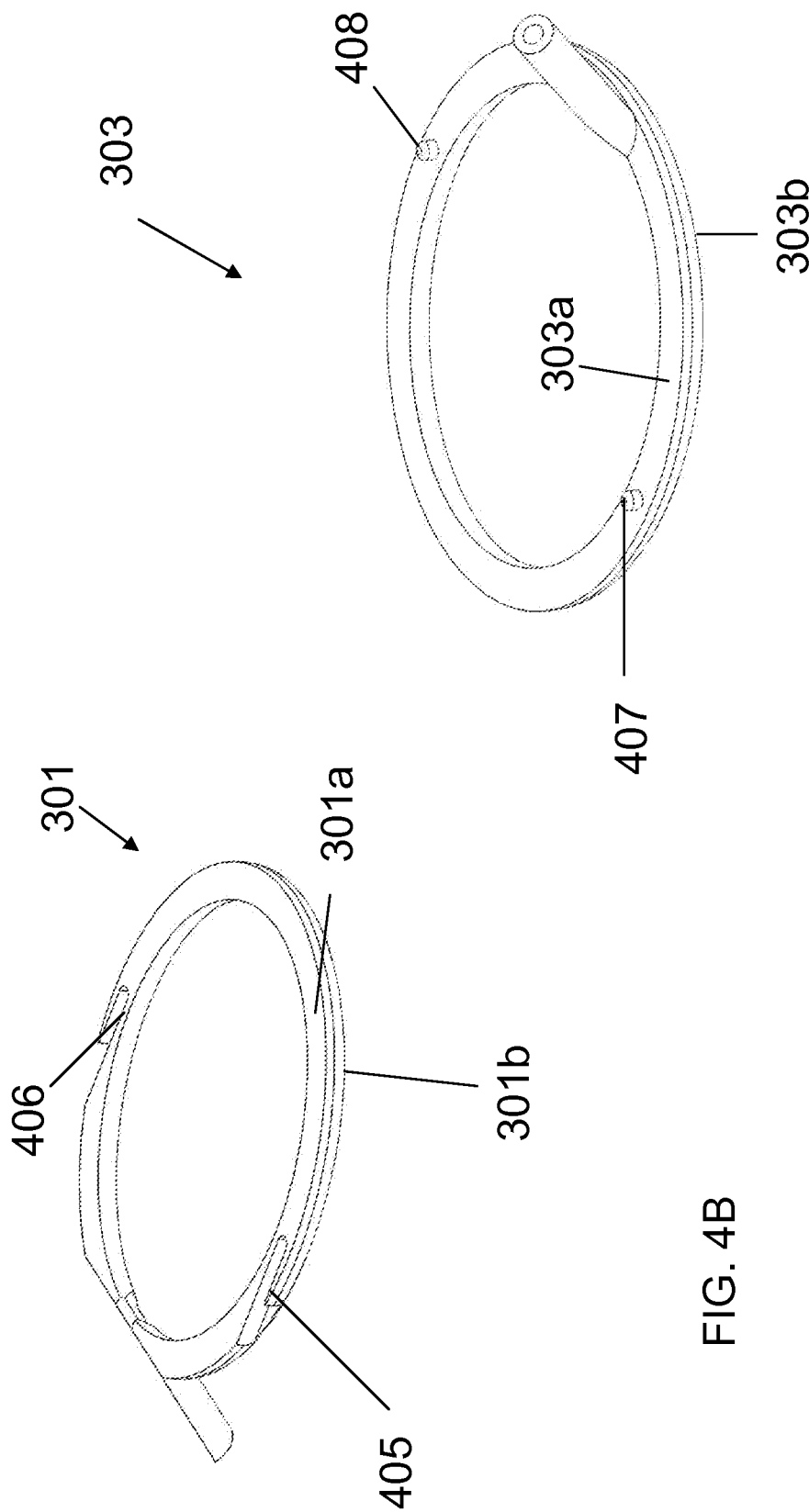

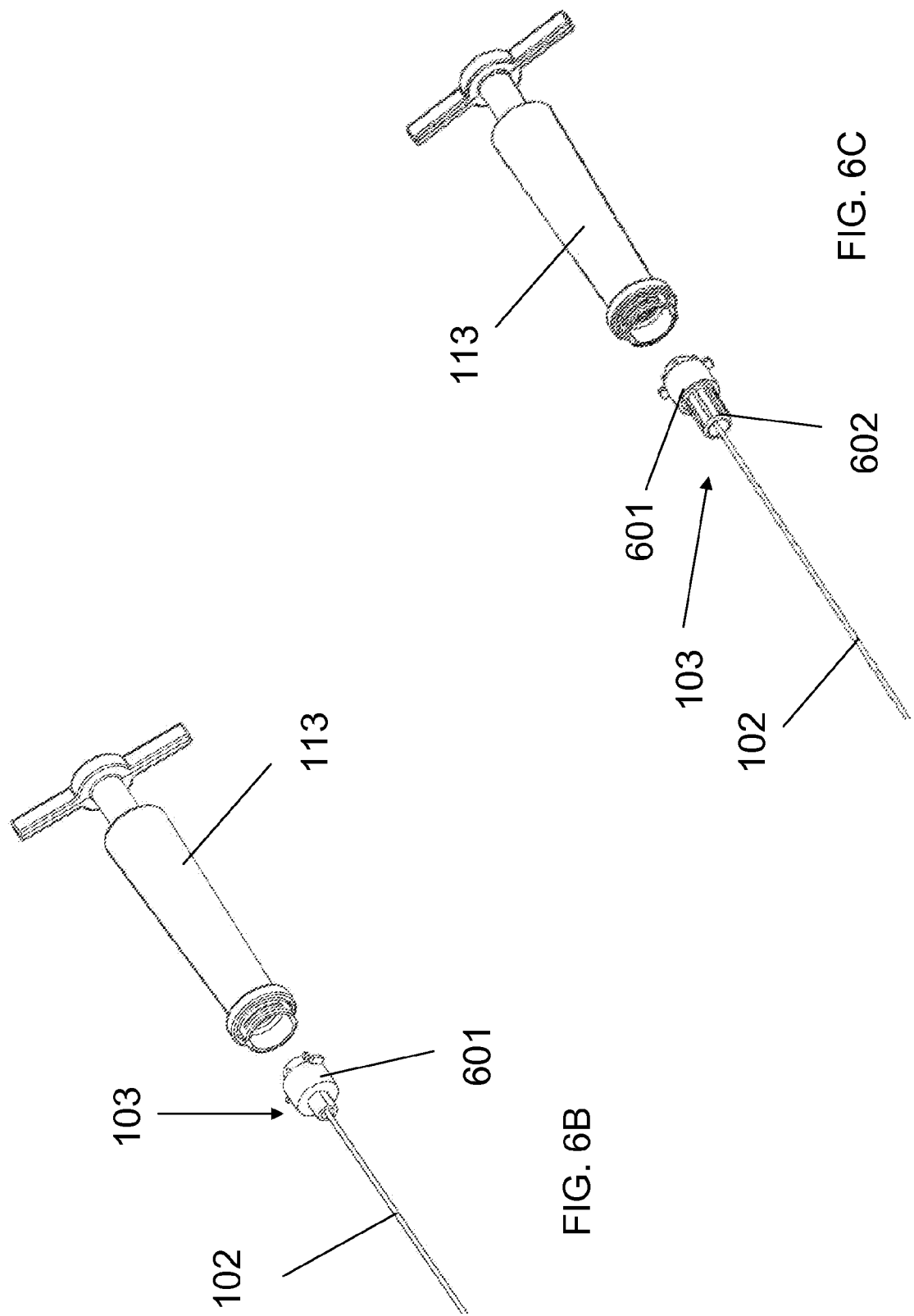

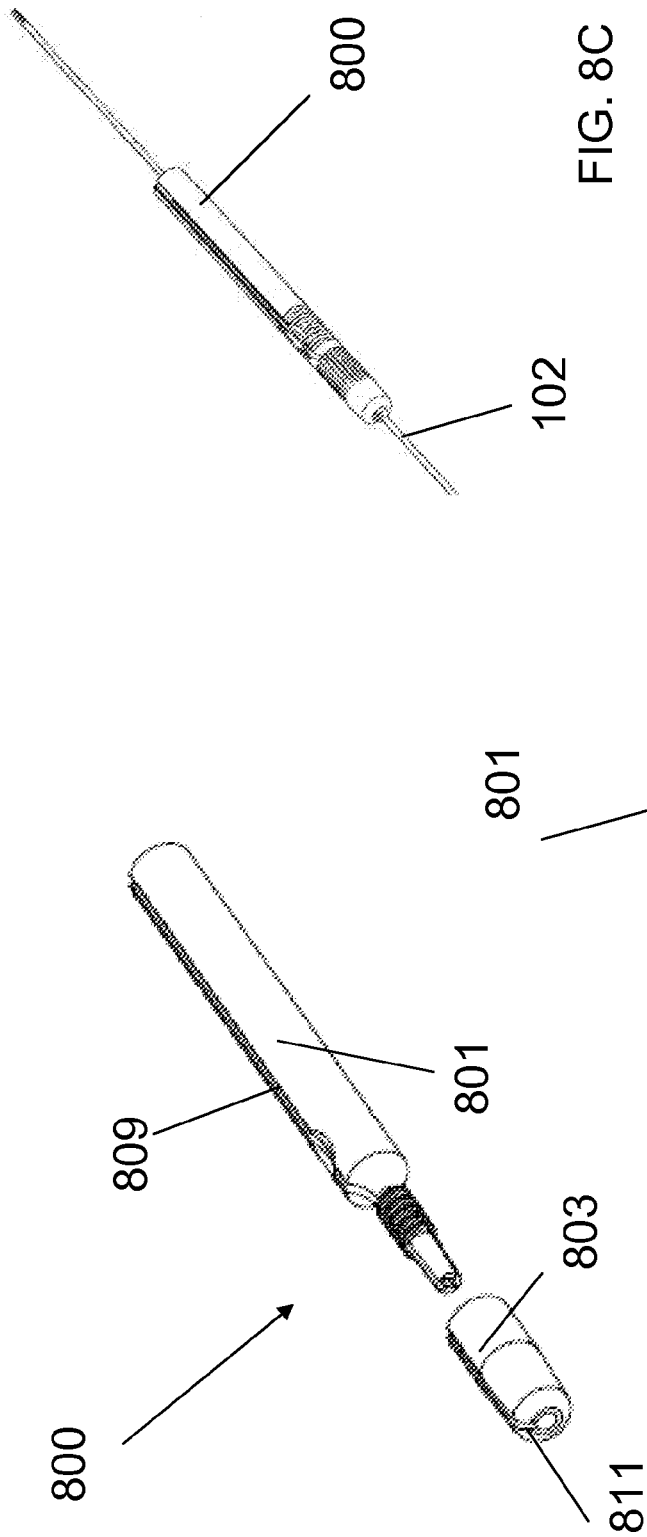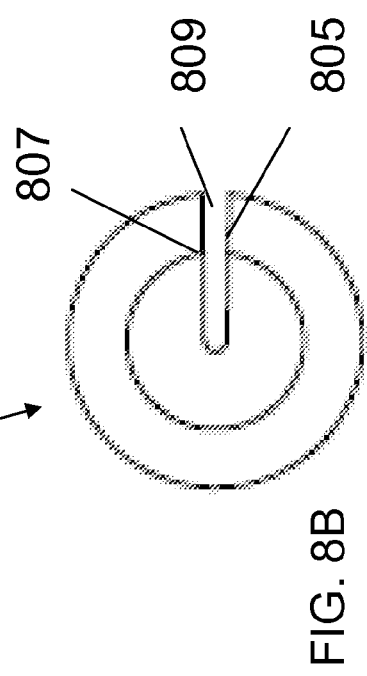
FIG. 8C
FIG. 8B
FIG. 8A

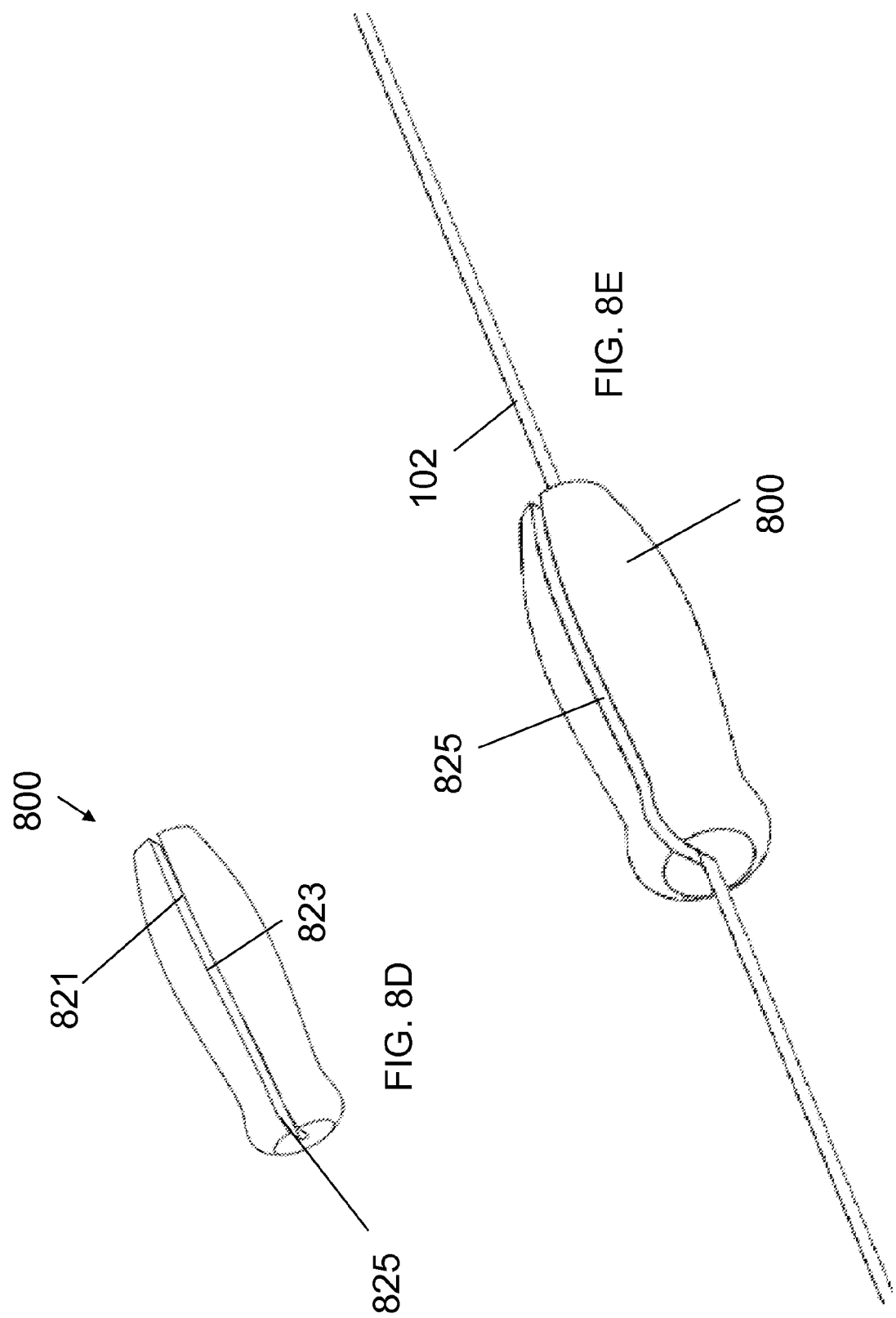

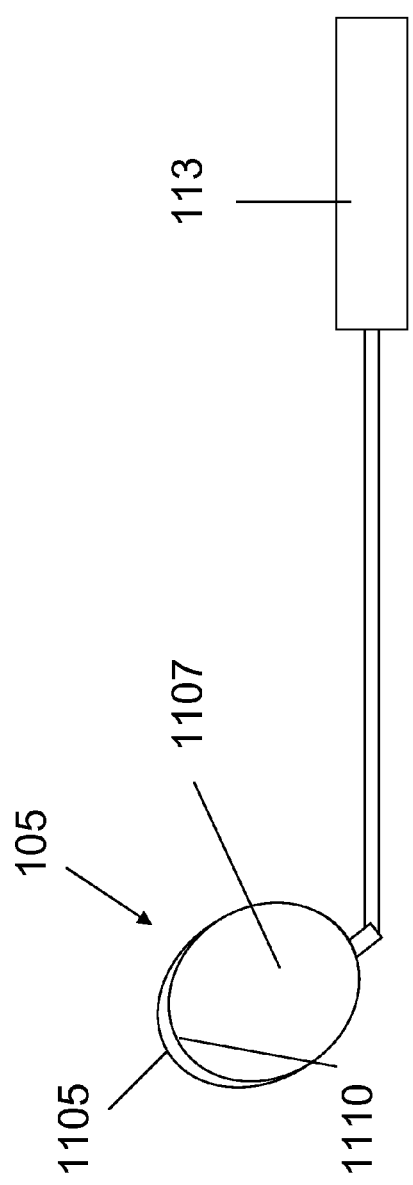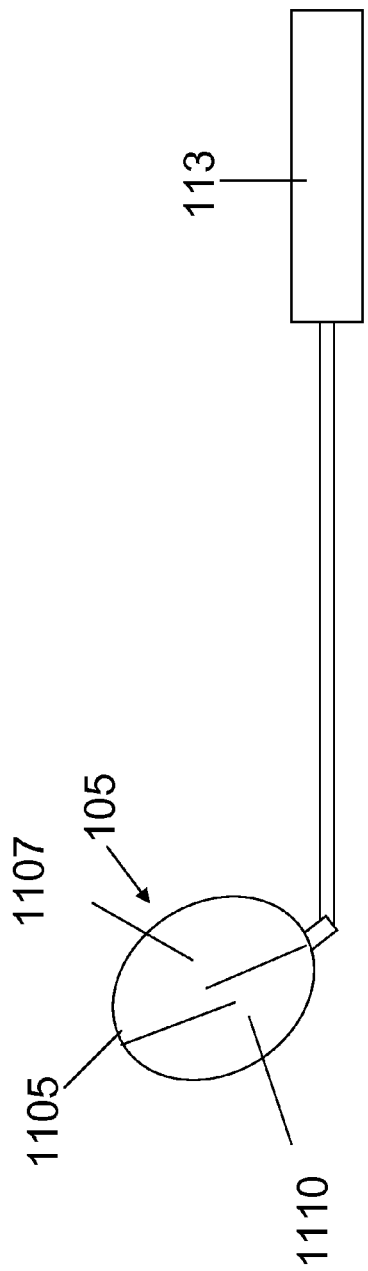
FIG. 11A
FIG. 11B

SYSTEMS AND METHODS FOR REMOTE ENDARTERECTOMY

RELATED APPLICATIONS

This application claims the benefit of and priority to U.S. Provisional Patent Application No. 61/432,866, filed on Jan. 14, 2011, the entirety of which is hereby incorporated herein by reference for the teachings therein.

FIELD

The presently disclosed embodiments relate to devices for the treatment of blood vessels, and more particularly to devices for performing remote endarterectomy.

BACKGROUND

Narrowing or occlusions (thromboses) of blood vessels has dangerous consequences for the health, because the quantity of blood able to flow through narrowed or occluded blood vessels is drastically reduced. Blood vessels may be narrowed or occluded due to an accumulation and swelling in artery walls that is made up of macrophage cells, or debris, that contain lipids (cholesterol and fatty acids), calcium and a variable amount of fibrous connective tissue, known as an atheroma. In order for effective blood circulation to occur and to avoid possible long term adverse effects, a blockage or obstacle in a blood vessel should be removed. Endarterectomy is a surgical procedure to remove the atheromatous plaque material, or plaque core, in the lining of a blocked artery. Endarterectomy is carried out by separating the plaque core from the arterial wall and removing the dissected plaque core from the patient's body.

SUMMARY

Systems and methods for remote endarterectomy are provided. According to aspects disclosed herein, there is provided a device for remote endarterectomy that includes an elongated member, having a proximal end, a distal end, and a longitudinal axis therebetween; an endarterectomy unit at the distal end of the elongated member formed by a first member engaged to a second member in a substantial secure alignment with the second member, wherein the endarterectomy unit has a circumferential enclosure configured to separate a plaque core from a blood vessel and an open region surrounded by the enclosure and configured to receive the separated plaque core therethrough; and an actuator coupled to the proximal end of the elongated member for translating the first member relative to the second member across the open space to transect the plaque core received in the open space.

According to aspects illustrated herein, there is provided a method for remote endarterectomy of an occluded blood vessel that includes placing an endarterectomy unit engaging a distal end of an elongated member into the occluded vessel, wherein the endarterectomy unit comprises a first member and a second member slidable with respect to one another; directing an exposed end of the plaque core into an open space of the endarterectomy unit defined by a circumferential enclosure; advancing the endarterectomy unit through the occluded blood vessel to dissect a length of the plaque core from the wall of the occluded blood vessel by the enclosure; maintaining the first member and the second member in substantial secure alignment with one another throughout the dissection of the plaque core; remotely severing the length of the plaque core by causing the first member and the second member to slide relative to one another across the open space of the endarterectomy unit to sever the plaque core; and removing the severed plaque core and the endarterectomy unit from the vessel.

According to aspects illustrated herein, there is provided a kit for remote endarterectomy that includes an endarterectomy unit disposed at a distal tip of an elongated member, wherein the endarterectomy unit is formed by a first member engaging a second member in a substantial secure alignment with the second member; and wherein the endarterectomy unit has a circumferential enclosure configured to separate the plaque core from the blood vessel and an open region surrounded by the enclosure and configured to receive the separated plaque core therethrough; and an actuator to be releasably attached to a proximal end of the elongated member via a hub for translating the first member and the second member relative to one another across the open space so as to transect the plaque core received in the open space.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A is a perspective close-up view of an endarterectomy unit of a device for remote endarterectomy of the present disclosure.

FIG. 2B is a cross-sectional view of a circumferential enclosure of a device for remote endarterectomy of the present disclosure.

FIG. 3B and FIG. 3C are front view and side view, respectively, of an embodiment endarterectomy unit of a device for remote endarterectomy of the present disclosure formed by a proximal member and distal member, wherein the proximal member and the distal member are shown held together as a unit.

FIG. 3D and FIG. 3E illustrate an embodiment proximal member and an embodiment distal member, respectively, of an embodiment endarterectomy unit of a device for remote endarterectomy the present disclosure.

FIG. 3F is a cross sectional view of an embodiment endarterectomy unit of a device for remote endarterectomy the present disclosure.

FIG. 4B and FIG. 4C are perspective close-up views of an embodiment of interlocking proximal member and distal member, respectively, of an embodiment endarterectomy unit a device for remote endarterectomy of the present disclosure.

FIG. 6B and FIG. 6C illustrate various embodiments of a hub for attaching an elongated member to an actuator of a device for remote endarterectomy of the present disclosure.

FIGS. 8A-8C illustrate an embodiment of a torque device suitable for use with a device for remote endarterectomy of the present disclosure.

FIGS. 8D-8E illustrate another embodiment of a torque device suitable for use with a device for remote endarterectomy of the present disclosure.

FIG. 11A and FIG. 11B illustrate embodiments of an endarterectomy unit of a device for remote endarterectomy of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
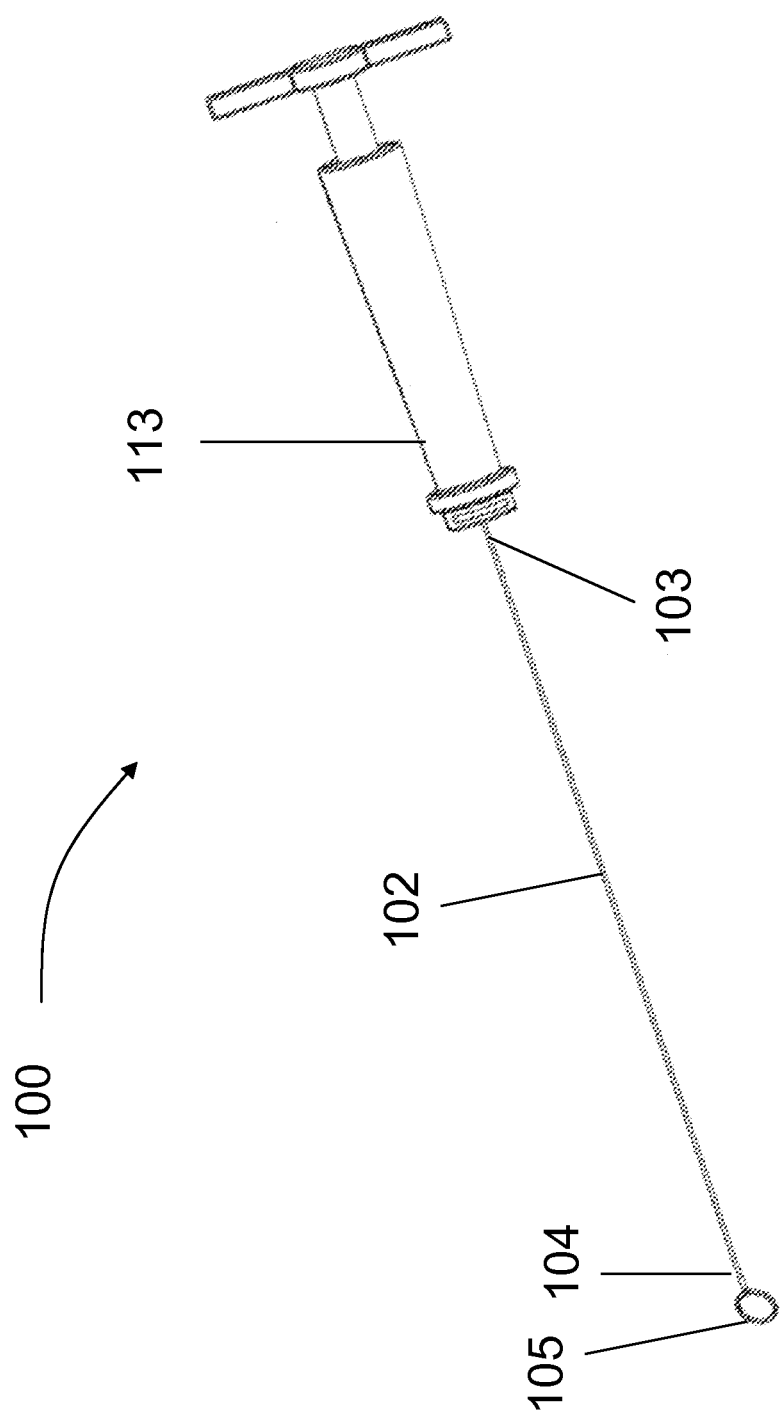
FIG. 1 is a perspective view of an embodiment of a device for remote endarterectomy of the present disclosure.

FIG. 1 illustrates an embodiment of a device 100 for remote endarterectomy. The device 100 includes an elongated member 102 with a proximal end 103, a distal end 104, and a longitudinal axis therebetween. The distal end 104 of the elongated member 102 terminates in an endarterectomy unit 105. An actuator 113 is disposed at the proximal end 103 of the elongated member 102. The actuator 113 is operably coupled to the endarterectomy unit 105 to control the operation of the endarterectomy unit 105.

Blood vessel blockages are typically found within the intima of a blood vessel, the thin innermost layer of a blood vessel. In an embodiment, the endarterectomy unit 105 is sized and shaped for insertion between intima together with the plaque core (collectively, "plaque core") and the wall of a blood vessel. The endarterectomy unit 105 is further configured to dissect the a length of plaque core away from the wall of a blood vessel, as well as to transect and remove the dissected plaque core from the blood vessel. Because the device 100 is capable of dissecting the plaque and transecting and removing the dissecting, the device 100 eliminates the need to use separate instruments for each step of the remote endarterectomy procedure. In this manner, the endarterectomy procedure can be performed quicker, decreasing impact of the procedure on the patient as well as the medical staff.

In reference to FIG. 2A, the endarterectomy unit 105 has a circumferential enclosure 107 enclosing an open region 109. The circumferential enclosure 107 includes an attachment region 119 at which the endarterectomy unit 105 attaches to the elongated member 102 and a free region 121 in opposing relation to the attachment region 119. In an embodiment, the endarterectomy unit 105 is mounted to the elongated member 102 at an angle selected as to ensure an effective dissecting and transecting of the plaque core. In an embodiment, the endarterectomy unit 105 is mounted to the elongated member 102 at an angle between about 35° and about 55°. In an embodiment, the endarterectomy unit 105 is mounted to the elongated member 102 at an angle of about 45°.

By way of a non-limiting example, for the endarterectomy unit 105 having an oval shape and mounted at the angle of 45°, the following endarterectomy unit diameters, with respect to the inner diameter of the blood vessel, may be employed:

| INNER DIAMETER OF BLOOD VESSEL | MAJOR INNER DIAMETER OF ENDARTERECTOMY UNIT |
| --- | --- |
| 3 mm | 5.5 mm |
| 4 mm | 6.5 mm |
| 5 mm | 7.5 mm |
| 6 mm | 8.5 mm |
| 7 mm | 9.5 mm |
| 8 mm | 10.5 mm |
| 9 mm | 11.5 mm |
| 10 mm | 12.5 mm |

In reference to FIG. 2B, the circumferential enclosure 107 has a cross-section configured to both be able to dissect the plaque core from the blood vessel and to transect the dissected plaque core. The circumferential enclosure 107 has an outer edge 115 and an inner edge 117. The outer edge 115 is smooth or rounded so as to enable the endarterectomy unit 105 to peel the plaque core from the blood vessel. In an embodiment, the circumferential enclosure 107 is oval-shaped having a major axis 111a and a minor axis 111b. In an embodiment, the minor axis 111b of the endarterectomy unit 105 may be about 2 mm smaller than the major axis 111a. In an embodiment, the endarterectomy unit 105 is provided with an oval shape to further assist the endarterectomy unit 105 in dissecting the plaque core from the blood vessel. Moreover, during the dissection of the plaque core, an oval-shaped endarterectomy unit 105 may apply asymmetric force on the blood vessel to minimize or completely eliminate potential impact on the blood vessel. As the plaque core is dissected from the blood vessel, the plaque core is directed into the open region 109 surrounded by the circumferential enclosure 107 and configured to receive the separated plaque core therethrough. In an embodiment, the inner diameter of the endarterectomy unit 105 may range between about 5 mm to about 13 mm. In an embodiment, the inner edge 117 includes one or more beveled sections, as is described below, so as to facilitate the transection of the plaque core received in the open region 109.

Figure 3A:
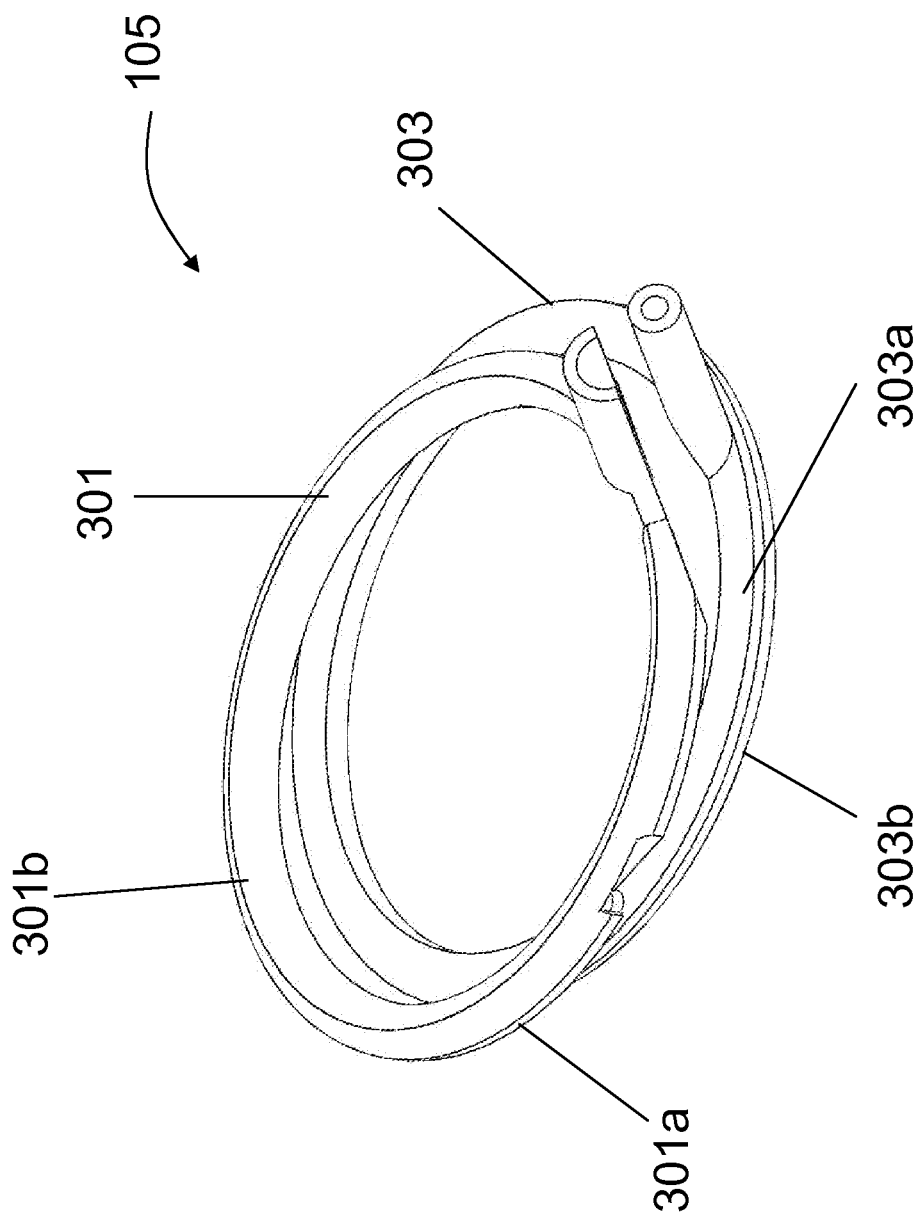
FIG. 3A is a perspective close-up view of an embodiment endarterectomy unit of a device for remote endarterectomy of the present disclosure formed by a proximal member and distal member, wherein the proximal member and the distal member are separated.

In an embodiment, to allow the endarterectomy unit 105 to transect and remove the plaque core from the vessel, the endarterectomy unit 105 is formed by a proximal member 301 and a distal member 303, as shown in FIG. 3A. Each member 301, 303 has an inner surface 301a, 303a and an outer surface 301b, 303b, respectively. The members 301, 303 meet at the inner surfaces 301a and 302a, which are flattened to permit the member 301, 303 to conformally fit together to form the endarterectomy unit 105, as shown in FIG. 3B and FIG. 3C. In an embodiment, the outer edges of the members 301, 303 are rounded and symmetric such that when the members 301, 303 are fitted together the outer edge 115 of the endarterectomy unit 105 is rounded and smooth, as shown in FIG. 3B and FIG. 3C, so as to enable the endarterectomy unit 105 to dissect the plaque core from the blood vessel and to do so with minimal adverse effect on the blood vessel.

In an embodiment, the inner edges of the members 301, 303 are asymmetric such that when the members 301, 303 are fitted together at least a section of the inner edge 115 of the endarterectomy unit 105 is beveled. In an embodiment, the proximal member has a beveled section 311 disposed on the inside edge of the proximal member 301 along a portion of the attachment region 119, as shown in FIG. 3D. In an embodiment, the distal member 303 has a beveled section 313 disposed along the inside edge of the distal member 303 along a portion of the free region 121, as shown in FIG. 3E. In an embodiment, the bevel is between about 35° and about 55°. In an embodiment, the beveled sections extend for about 180°. As shown in FIG. 3F, which is a cross-sectional view of the endarterectomy unit 105 along the major axis 111a, the beveled sections 311 and 313 are located on the outer surfaces of the proximal member 301 and the distal member 313, such that the beveled sections 311, 313 face in opposite direction away from one another. When transecting the plaque core, because the beveled section 311 and 313 are in the opposing relation to one another, the movement of the proximal member 301 and the distal member 303 relative to one another across the open space 109 of the endarterectomy unit 105, as is discussed below, results in a highly efficient shear, scissor-like cutting action. In an embodiment, as the beveled sections 311, 313 cut through the plaque core, the opposing edge holds the plaque core, thereby resulting in a scissor-like cutting action. In an embodiment, only one of the member 301, 303 has a beveled section and the other member 301, 303 has a flat section opposite the beveled section. It should further be noted that other variations are possible as long as the endarterectomy unit 105 is provided with capability to transect the plaque core.

In an embodiment, the proximal member 301 engages the distal member 303, or vice versa, so the proximal member 301 and the distal member 303 remain in a substantial alignment with one another. In this manner, the proximal member 301 and the distal member 303 act as a unitary structure throughout the dissecting step to prevent, or at least minimize, inadvertent damage to the blood vessel. During the dissecting step, the user may need to apply considerable force on the device 100 in order to be able to advance the device 100 and to dissect the plaque core from the blood vessel. This force exerted on the endarterectomy unit 105 may cause the proximal member 301 and the distal member 303 to translate radially or torsionally with respect to one another, which may cause damage to the blood vessel. The members 301, 303 are designed to resist radial and torsional forces to remain in a substantial alignment with one another to act as a unitary structure throughout the dissecting step, as shown in FIG. 3B and FIG. 3C. Because the proximal members 301 and the distal member 303 remain in radial and torsional alignment, the outer edge 115 of the endarterectomy unit 105 is maintained smooth and rounded during the dissecting step to aid the endarterectomy unit 105 in dissecting the plaque core from the blood vessel, while preventing or at least minimizing injury to the blood vessel The problem of possible misalignment of the proximal member 301 and the distal member 303 of the endarterectomy unit 105 is unique to the devices of the present disclosure, because the devices of the present disclosure are simultaneously designed to dissect the plaque core away from the wall of a blood vessel, as well as to transect and remove the plaque core from the blood vessel. Devices exist for dissecting the plaque core from the wall of a blood vessel. Prior art dissectors typically include a single-piece dissector units because these devices are not used for transecting and/or removing the plaque core. Because these devices have a single-piece dissector, these devices do not suffer from the problem of possible misalignment of individual pieces forming the dissector. Moreover, devices exist for transecting and/or removing the plaque core, but these devices are not designed to dissect the plaque core from the wall of a blood vessel, and thus are not used in that manner. The prior art devices for plaque core transecting may include multiple transecting rings movable relative to one another, however, because prior art devices for plaque core transecting are typically used to only cut and remove the already-dissected core, rather than dissect the plaque core, forces experienced by prior art devices for plaque core transecting are much smaller than the forces experienced by the devices of the present disclosure. Therefore, misalignment of individual transecting rings is not of concern in the prior art devices for plaque core transecting, and thus the prior art devices for plaque core transecting do not need to include design features to ensure that the individual rings remain in substantial alignment during the procedure.

Figure 4A:
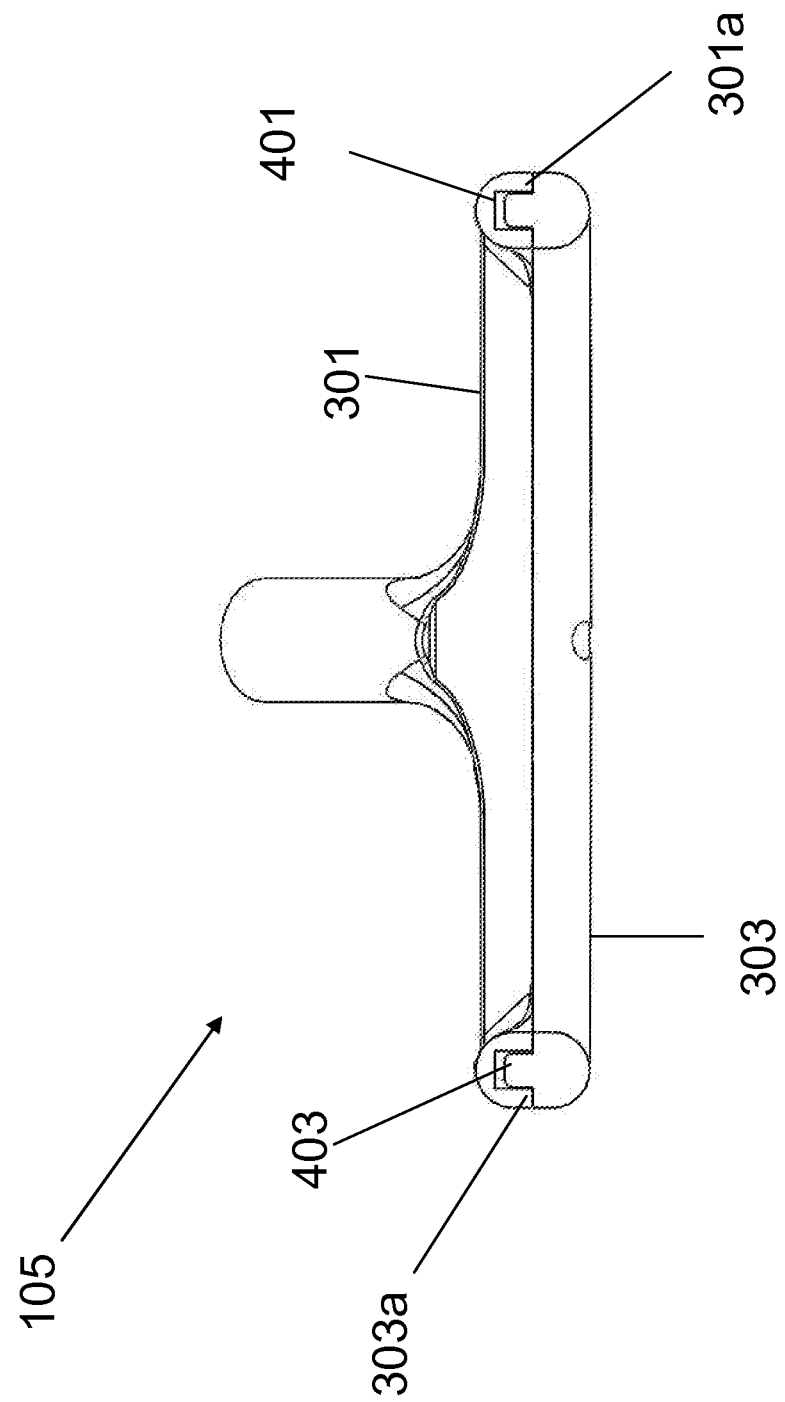
FIG. 4A is a cross-sectional view of an embodiment endarterectomy unit a device for remote endarterectomy of the present disclosure formed by interlocking proximal member and distal member.
Figure 4D:
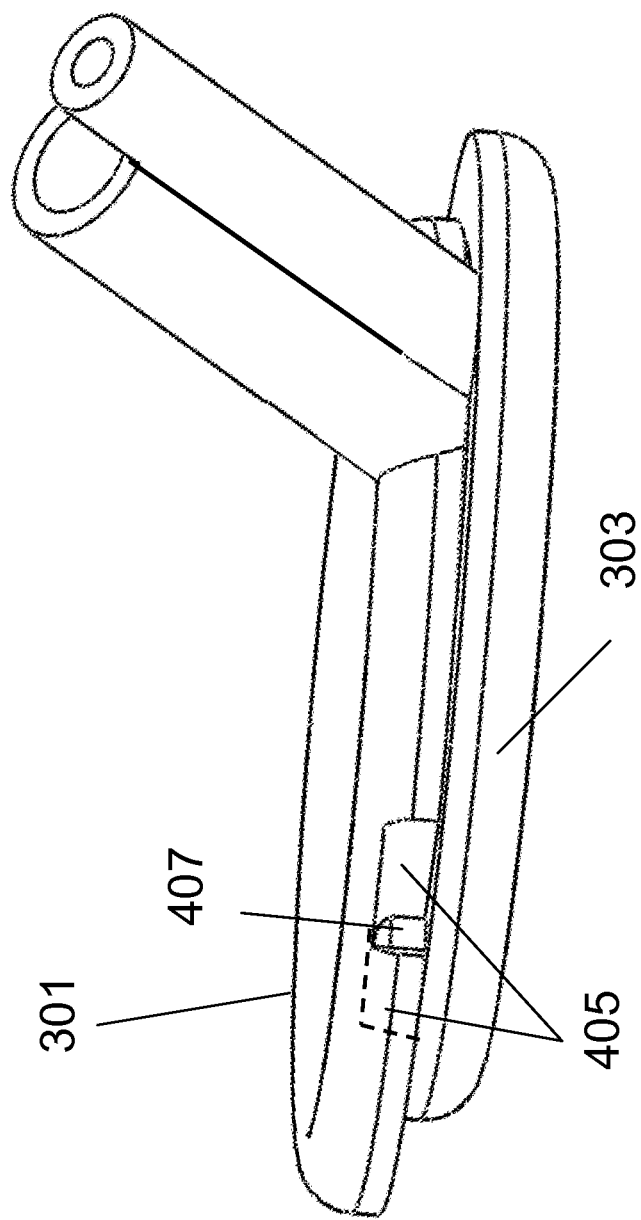
FIG. 4D is a perspective close-up view of an endarterectomy unit a device for remote endarterectomy of the present disclosure, formed with interlocking proximal member and distal member.

Referring to FIGS. 4A-4D, in an embodiment, to maintain substantial alignment between the proximal member 301 and the distal member 303 during the dissecting step, the proximal member 301 and the distal member 303 are interlocked. As shown in FIG. 4A, the proximal member 301 and the distal member 303 include a first 401 and a second 403 cooperating structures, respectively, configured to join together to maintain the members 301, 303 in a substantial alignment relative to one another. In an embodiment, the first and second cooperating structures also guide the movement of the member 301 and 303 relative to one another. In an embodiment, channels 405, 406 may be cut into the inner surface 301a of the proximal member 301, as shown in FIG. 4B, and corresponding posts 407, 408 may be provided on the inner surface 303a of the distal member 303, as shown in FIG. 4C, to be slidably inserted into the channels 405, 406. When the proximal member 301 and the distal member 303 are in the initial dissecting position for the insertion of the endarterectomy unit 105 into a blood vessel and dissection of the plaque core, the posts 407, 408 may be positioned in the top of the corresponding channels 405, 406, thus locking the proximal member 301 and the distal member 303 in alignment, as shown in FIG. 4D, such that the rounded or smooth outer edge 115 is maintained throughout the dissection. In another embodiment, rails could be used in place of the posts 407, 408 on the distal member 303 for alignment and locking with the proximal member 301. It should of course be understood that the distal member 303 may include the channels 405, 406, while the proximal member 301 may include the corresponding posts 407, 408 or rails. Alternatively or additionally, the proximal member 301 and the distal member 303 may also be pre-tensioned toward each other to keep the proximal member 301 and the distal member 303 aligned during the dissecting step. Various other means may be employed to prevent axial or torsional misalignment of the proximal member 301 and the distal member 303 with respect to one another and to keep the members 301, 303 in a substantial alignment with one another during the dissecting step.

Figure 5:
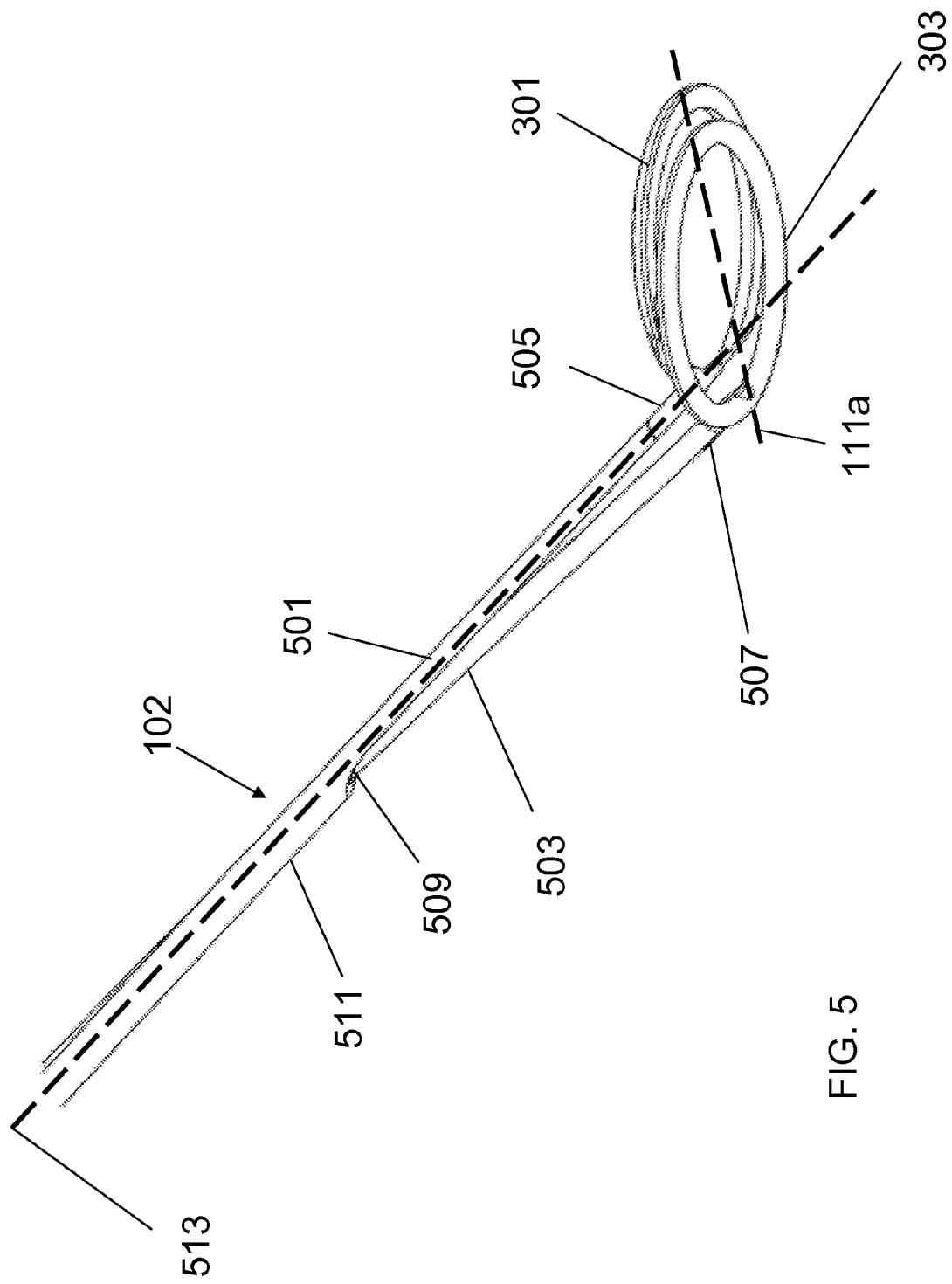
FIG. 5 illustrates an embodiment of an elongated member of a device for remote endarterectomy of the present disclosure.

In an embodiment, the proximal member 301 and the distal member 303 are slidable with respect to one another. In references to FIG. 5, in an embodiment, when actuated, the distal member 303 slides relative to the proximal member 301 to traverse the open space 109 of the endarterectomy unit 105 to cut the plaque core received in the open space. As shown in FIG. 5, in an embodiment, the distal member 303 slides relative to the proximal member 301 substantially along the major axis 111a of the distal member 303 and in transversely to the longitudinal axis 513 of the elongated member 102. The proximal member 301 and the distal member 303 may slide with respect to one another from an initial dissecting position, in which the proximal member 301 and the distal member 303 are in a substantial alignment with one another, to an intermediate translated position, in which the proximal member 301 and the distal member 303 are partially translated along the central axis 111 with respect to one another, to a final transected position, in which the proximal member 301 and the distal member 303 are fully translated along the central axis 111 with respect to one another.

Referring to FIG. 5, to permit the movement of the proximal member 301 and the distal member 303 with respect to one another, in an embodiment, the elongated member 102 comprises a shaft housing 501 and an actuating pin 503, with the proximal member 301 of the endarterectomy unit 105 being disposed at a distal end 505 of the shaft housing 501 and the distal member 303 being disposed at a distal end 507 of the actuating pin 503, such that movement of the actuating pin 503 with respect to the shaft housing 501 causes the distal member 303 and the proximal member 301 to translate with respect one another. In an embodiment, this design allows the proximal member 301 and the distal member 303 to translate back and forth between the initial dissection position, intermediate translated position, and fully translated position.

In an embodiment, the actuating pin 501 is slidably disposed within the shaft housing 501. The actuating pin 503 enters the shaft housing 501 at a proximal end (not shown) of the shaft housing 501 and exits out of the shaft housing 501 through an opening 509 on a bottom side 511 of the shaft housing 501. Upon exiting the opening 509, the actuating pin 503 extends substantially parallel to the shaft housing 501 to the distal end 104 of the elongated member 102 to attach to the distal member 303. In an embodiment (not shown), the actuating pin 503 is positioned adjacent to the shaft housing 501.

Figure 6A:
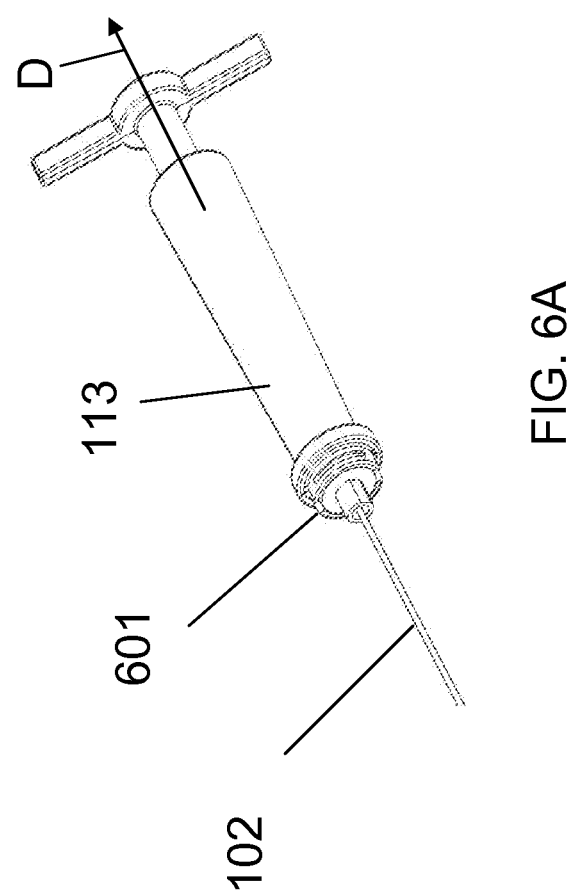
FIG. 6A is a perspective close-up view of the proximal end of a device for remote endarterectomy of the present disclosure.

As noted above, in an embodiment, the device 100 includes the actuator 113 operably coupled to the endarterectomy unit 105 for operating the endarterectomy unit 105. The actuator 113 acts to cause the movement of the proximal member 301 and the distal member 303 with respect to one another. In reference to FIG. 6A, in an embodiment, a hub 601 may be disposed at the proximal end 103 of the elongated member 102 for releasably attaching the actuator 113 to the elongated member 102. The actuator 113 is detachable to remove excess proximal weight during the dissecting step, when the actuator 113 is not used. FIG. 6B and FIG. 6C illustrate various embodiments of the hub 601. In an embodiment, as shown in FIG. 6C, the hub 601 has an extended gripping area 602 in the distal section of the hub 601 to allow for easier gripping for the user to attach and lock the hub 601 to the actuator 113.

Figure 6D:
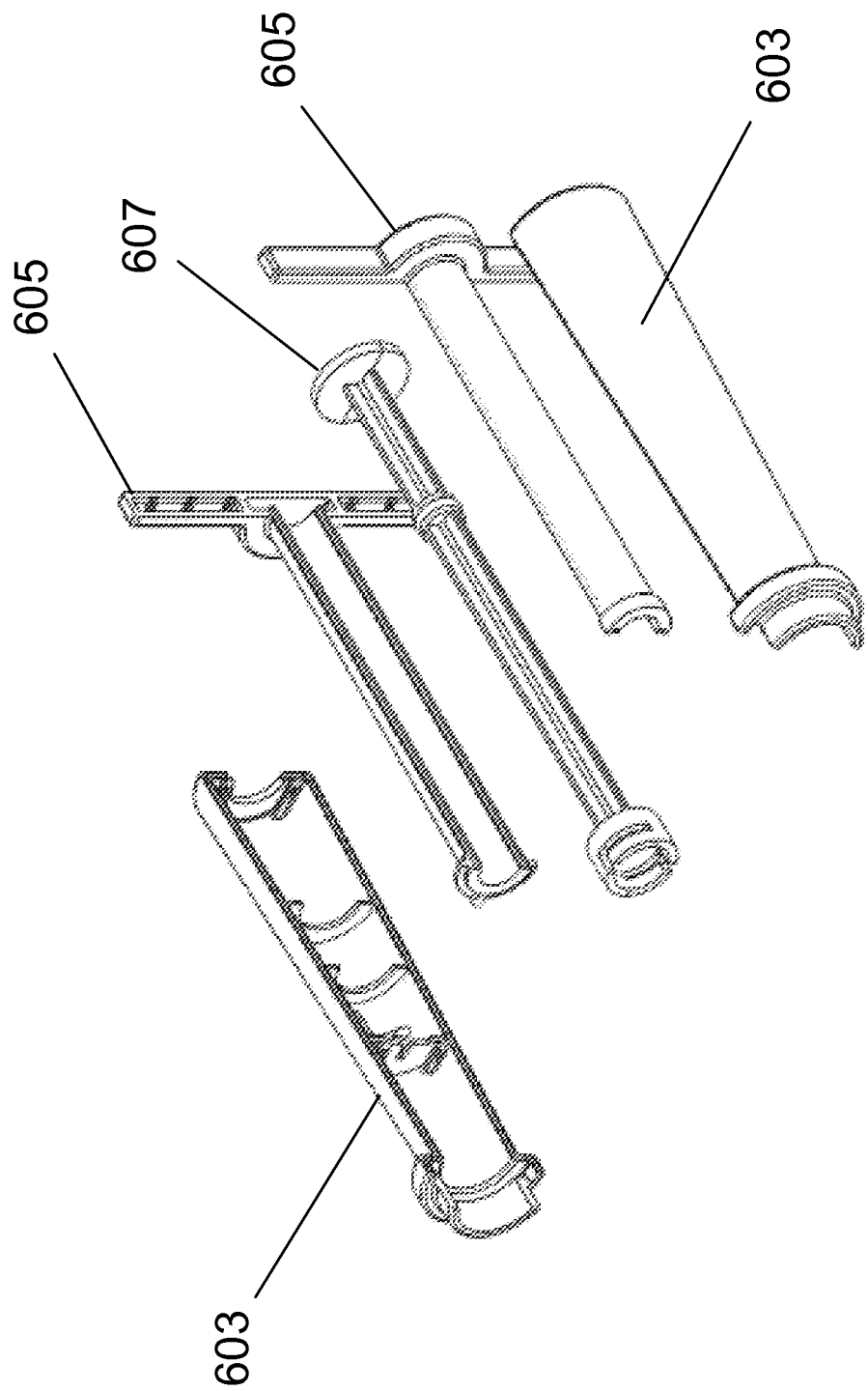
FIG. 6D and FIG. 6E are exploded views of various embodiments of an actuator of a device for remote endarterectomy of the present disclosure.
Figure 6E:
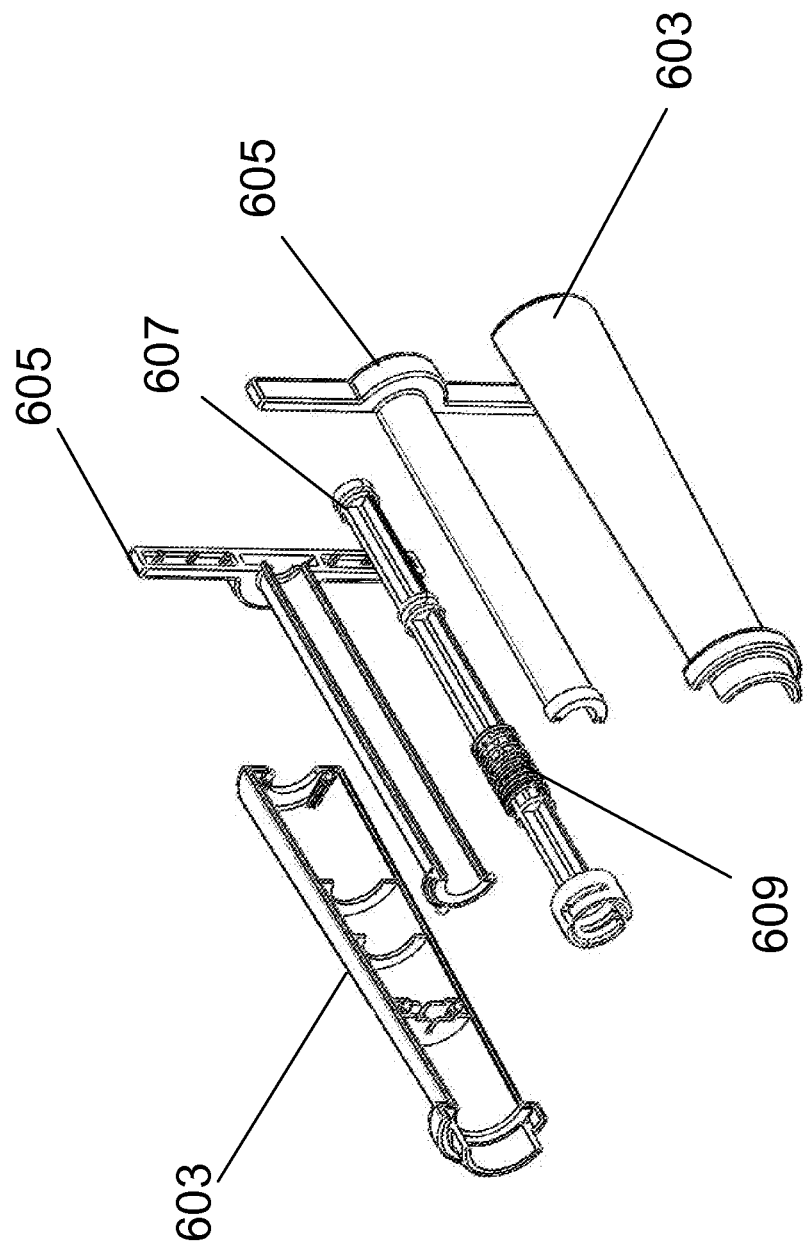

Referring to FIG. 6D, in an embodiment, the actuator 113 may comprise a two-component housing 603, a two-component handle 605 disposed within the housing 603, and a coupler 607 partially disposed within the handle 605. In an embodiment, the proximal end of the actuating pin 503 attaches to the coupler 607, thereby coupling the actuating pin 503 to the handle 605. In operation, pulling the handle 605 out of the housing 603 in the proximal direction, as indicated by the arrow D in FIG. 6B, also pulls the actuating pin 503 in the proximal direction to cause the distal member 303 to move along the central axis 111 of the proximal member 301 from the initial dissecting position toward the final transecting position. On the other hand, returning the handle 605 to its original position within the housing 603 also returns the distal member 303 to the initial dissecting position in alignment with the proximal member 301. In this manner, the device 100 of the present disclosure is able to make multiple cuts during the procedure, without the need to remove the device from the patient. In an embodiment, as shown in FIG. 6E, the actuator 113 includes a spring 609 disposed on the coupler 607. The spring 609 acts to keep the t-handle in the forward (distal) position to allow for attachment of the shaft/ring assembly.

The elongated member 102, including the shaft housing 501 and the actuating pin 503, are made from a biocompatible material. Because the device 100 is designed to be pushed through a blood vessel and to dissect plaque core from the blood vessel, the elongated member 102 may be sufficiently rigid along its longitudinal axis, while remaining sufficiently flexible in a radial direction from side to side. If the endarterectomy unit 105 of the device 100 encounters dense areas (calcification) within the plaque core, the elongated member 102 can preferably flex but not kink due to increased compressive loads. Suitable materials include, but are not limited to, stainless steel, titanium and titanium alloys, such as nitinol (NiTi). In an embodiment, the shaft housing 501 and the actuating pin 503 may be formed from stainless steel or nitinol hypotubes. Similarly, the endarterectomy unit 105, including the proximal member 301 and the distal member 303, may also be made from a biocompatible metal, such as stainless steel, titanium or titanium alloys, such as nitinol (NiTi).

Figure 7A:
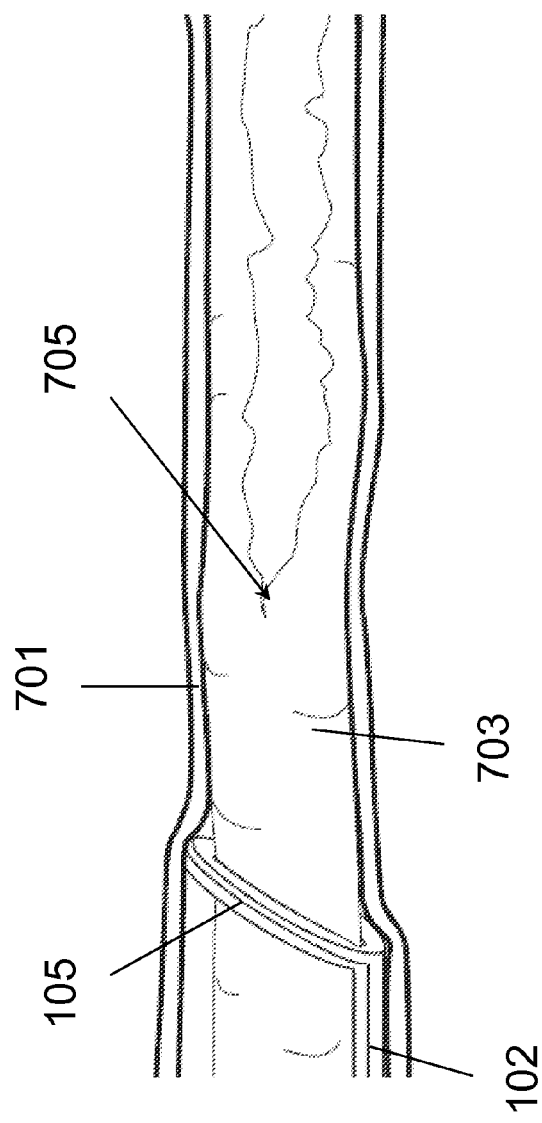
FIGS. 7A-7C show an embodiment of method steps for plaque removal with a device for remote endarterectomy of the present disclosure.
Figure 7B:
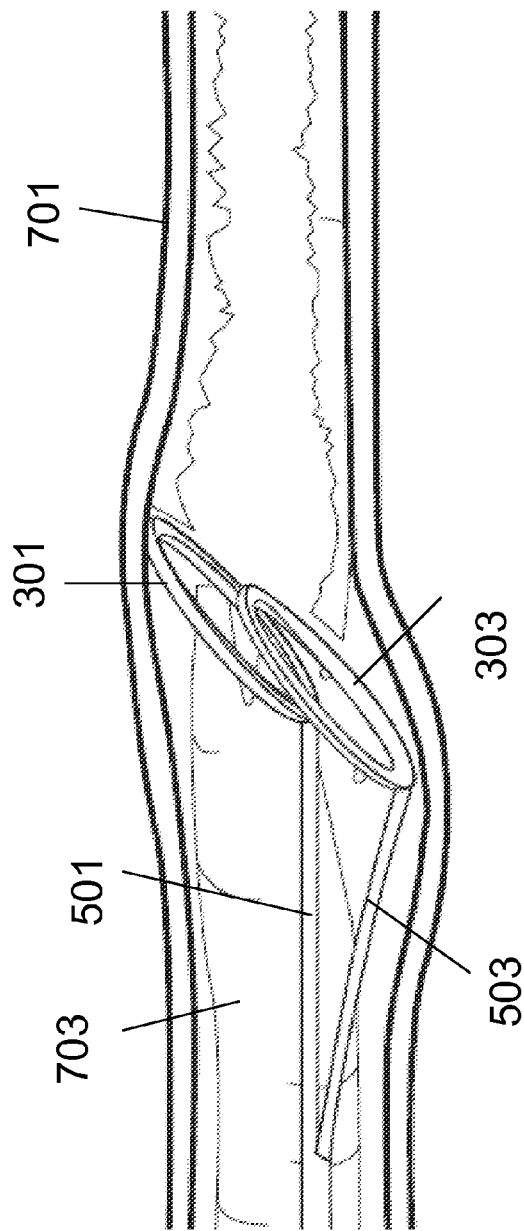
Figure 7C:
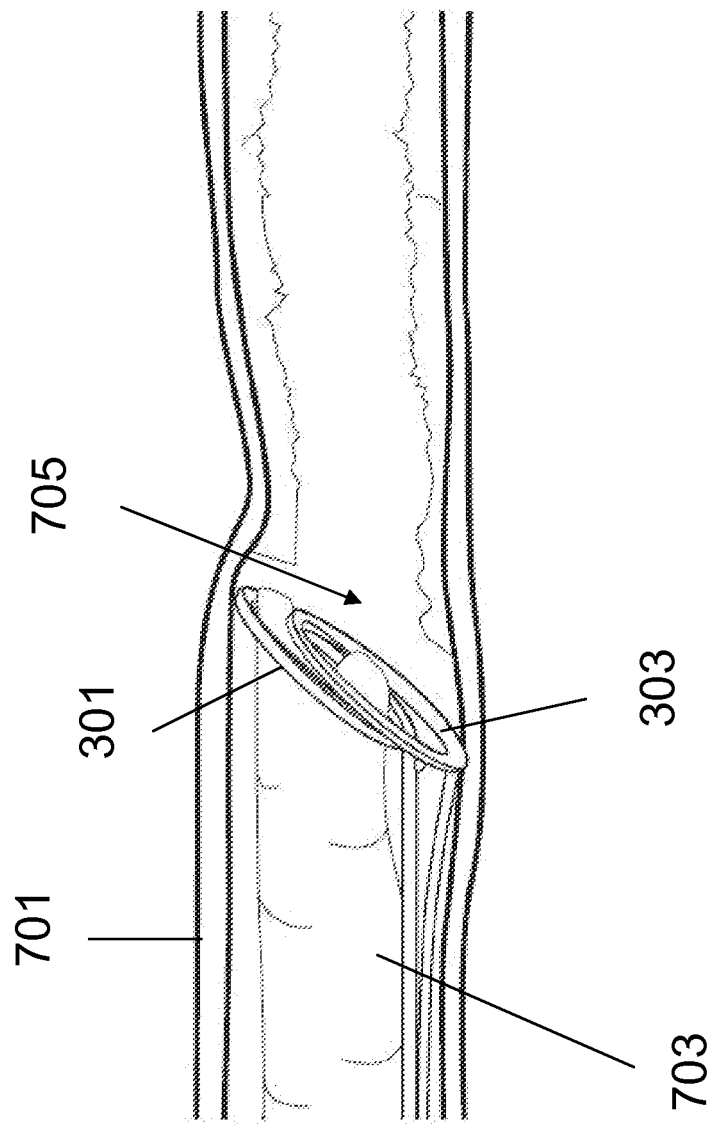

In operation, as shown in FIG. 7A, FIG. 7B and FIG. 7C, an occluded vessel 701 to be endarterectomized may initially be exposed and secured in place with sutures. An arteriotomy of the occluded vessel 701 may then be performed to expose a plaque core 703 and to establish a dissection plane around the plaque core 703. As shown in FIG. 7A, the elongated member 102 of the device 100 is inserted into the occluded vessel 701 and the endarterectomy unit 105 is placed in the dissection plane around the plaque core 703. The circumferential enclosure 107 is placed between the plaque core 703 and the wall of the occluded vessel 701 and the plaque core 703 is received within the open space 109. The endarterectomy unit 105 is then advanced along the occluded vessel 701 by pushing on the elongated member 102, optionally with a subtle twisting motion, to dissect the plaque core 703 from the occluded blood vessel 701, as shown in FIG. 7A. In FIG. 7A, the section of the plaque core 703 proximal of the endarterectomy unit 105 has been dissected from the occluded vessel 701, while the section of the plaque core 703 distal to the endarterectomy unit 105 is still attached to the occluded vessel 701. The endarterectomy unit 105 may be advanced along the occluded blood vessel 701 to continue dissecting the plaque core 703 from the occluded vessel 701 until the endarterectomy unit 105 reaches a desired position, such as a position 705 at the end of the plaque core 703.

In reference to FIGS. 8A-8E, to assist the user in controlling the device 100 during the dissecting step, the device 100 of the present disclosure may include a torque device 800. In an embodiment, the torque device 800 can be slidably and removably attached to the elongated member 102. In the beginning of the procedure, the torque device 800 may be securely attached by the user to the elongated member 102 of the device 100 in close proximity to the patient's body to permit fine manipulation of the device 100 by the user, while ensuring that the elongated member 102 does not kink. As the device 100 is advanced along the occluded blood vessel, the torque device 800 can be moved proximally along the elongated member 102 to provide additional length of the elongated member 102 between the patient's body and the torque device 800, so the endarterectomy unit 105 can be advanced further along the occluded vessel.

In an embodiment, as illustrated in FIG. 8A, the torque device 800 may comprise a gripping member 801 and a compression member 803, which can be side loaded onto the elongated member 102. The gripping member 801 includes opposed first and second gripping surfaces 805, 807, defining an open channel 809 through which the elongated member 102 may be positioned between the first and second gripping surfaces 805, 807, as shown in FIG. 8B. The compression member 803 also includes an open channel 811 configured to receive the elongated member 102, as shown in FIG. 8C. When the compression member 803 is engaged with the gripping member 801 the open channel 809 of the gripping member 801 may be in longitudinal alignment with the open channel 811 of the compression member 803 to receive the elongated member 102. The compression member 803 may threadably engage the gripping member 801 to control the movement of the first and second gripping surfaces 805, 807. The compression member 803 may be tightened about the gripping member 801 to cause the first and second gripping surfaces 805, 807 to grip the elongated member 102. On the other hand, the compression member 803 may be loosened about the gripping member 801 to move the first and second gripping surfaces 805, 807 apart to enable the user to slide the torque device 800 along the elongated member 102.

In another embodiment, as illustrated in FIG. 8D, the torque device 800 may be formed from a compliant material, such as thermoplastic elastomer, silicone, rubber or combinations thereof. In such an embodiment, the torque device 800 may include opposed first and second gripping surfaces 821, 823, which define an open channel 825 for positioning the elongated member 102 therein, as shown in FIG. 8E. Because the torque device is, in this embodiment, formed from a compliant material, the first gripping surface 821 and the second gripping surface 823 are biased toward each other to grip the elongated member 102 positioned in the open channel 825.

Referring back to FIGS. 7A-7C, when the endarterectomy unit 105 is at the desired position 705, the endarterectomy unit can be activated to transect the distal end of the plaque core 703, as shown in FIG. 7B. As described above, in an embodiment, pulling the handle 605 of the actuator 113 proximally toward the user causes the distal member 303 to translate with respect to the proximal member 301. In the embodiment of the device 100 where the elongated member 102 includes the shaft housing 501 and the actuating pin 503, pulling the handle 605 causes the actuating member 503 to move in the proximal direction such that the distal member 303 relative to the proximal member 301 to traverse open space 109 to transect the plaque core 703. The handle 113 is pulled until the plaque core 703 is completely severed, such as, for example, the proximal member 301 and the distal member 303 are in the final transected position. The severed plaque core 703 may be removed by removing the device 100 while keeping the proximal member 301 and the distal member 303 in the intermediate translated position, as illustrated in FIG. 7C, or by any other means.

Figure 9:
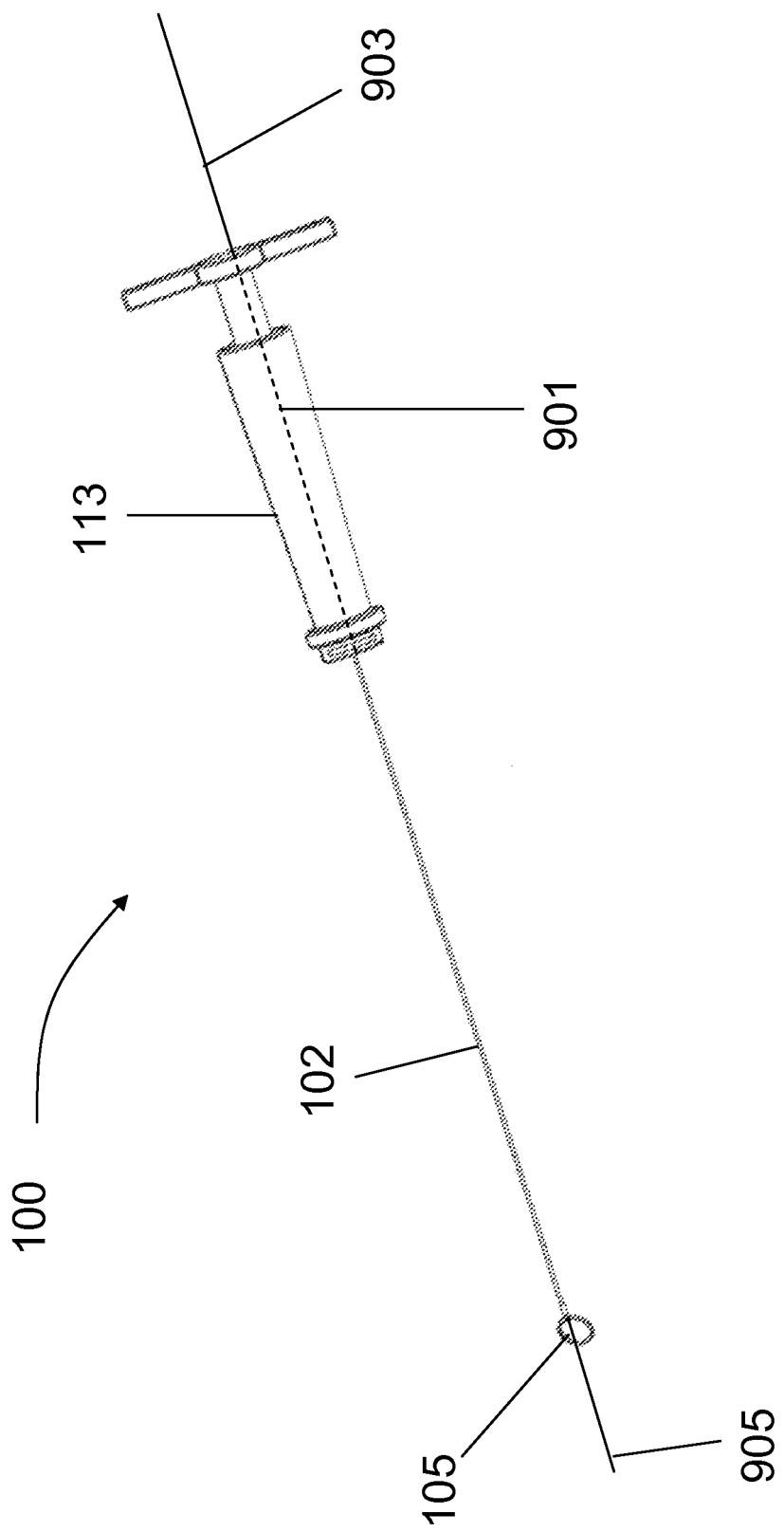
FIG. 9 illustrates a perspective view of an embodiment of a device for remote endarterectomy of the present disclosure.

In an embodiment, as illustrated in FIG. 9, the device 100 of the present disclosure may include a central lumen 901 extending longitudinally along the entire length of the device 100, including the actuator 113, the elongated member 102 and the endarterectomy unit 105. A guide wire 903 can be advanced through the central lumen 901 to position a distal tip 905 of the guide wire 903 beyond the endpoint of the removed plaque core. After extraction of the plaque core, the guide wire 901 can be left inside the vessel for a later use as a track for delivery of a stent and/or angioplasty balloon to push back the intimal flap, i.e. a loose end of the intima left behind after the intima surrounding the plaque core is transected, into the vessel wall to prevent the intimal flap from impeding blood flow or serving as a platform for thrombus formation and stenosis.

Figure 10:
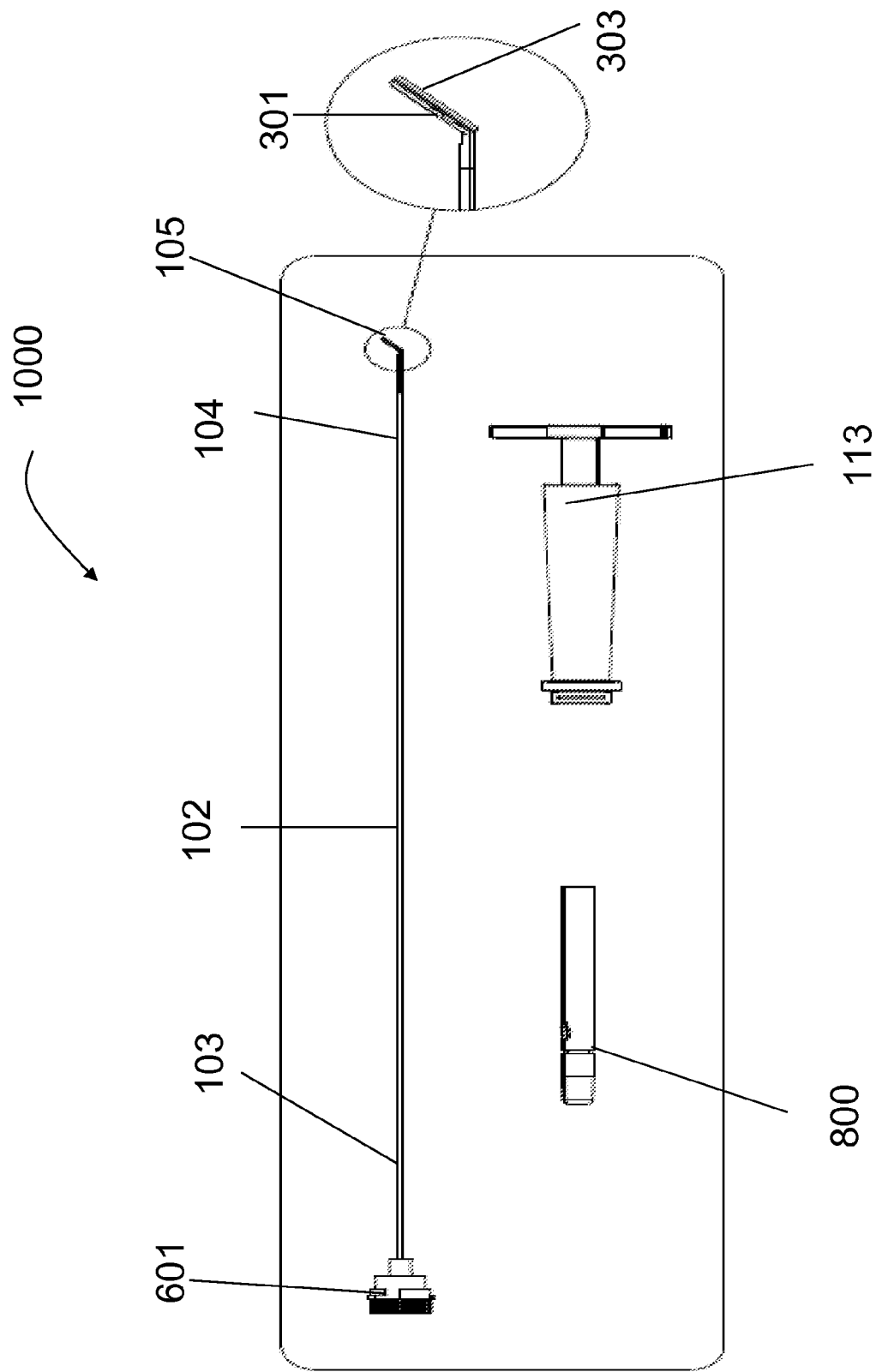
FIG. 10 is a perspective view of an embodiment of a kit for remote endarterectomy of the present disclosure.

FIG. 10 is a schematic illustration of an embodiment of a kit 1000 for performing a remote endarterectomy of the present disclosure. The kit 1000 may include an endarterectomy unit 105 disposed at a distal tip 104 of an elongated member 102. In an embodiment, the endarterectomy unit 105 may include a proximal member 301 and a distal member 303 translatable with respect to one another. The kit may further include an actuator 113 to be releasably attached to a proximal end 103 of the elongated member 102 via a hub 601. The actuator 113 may be used to translate the proximal member 301 and the distal member 303 translatable with respect to one another. In an embodiment, the kit 1000 may also include a torque device 800, which can be releasably and slidably attached to the elongated member 102 to permit fine manipulation of the endarterectomy unit 105 by the user.

FIG. 11A and FIG. 11B illustrate alternative embodiments of the endarterectomy unit 105. In an embodiment, the endarterectomy unit 105 may comprise a dissecting member 1105 and one or more transecting members 1110. The dissecting member 1105 is sized and shaped so the dissecting member defines an open space 1107 through which the plaque core can pass. The dissecting member 1105 is configured to dissect the plaque core away from the blood vessel. In an embodiment, to achieve this goal, the dissecting member 1105 may be substantially oval. The transecting member 1110 may be housed in or along an edge of the dissecting member 1105 during the dissecting step and may be activated using an actuator 113 to sever the plaque core when the endarterectomy unit 105 is in a desired position along the blood vessel, such as at or near the end of the blockage. The transecting member may be constructed to sever the plaque core by virtue of its size, shape, surface character or combinations thereof. For example, the transecting member 1110 may have a sharpened edge or sharp particles coating its surface. In an embodiment, the transecting member may comprise a wire configured to pass through the open space 1107 of the dissecting member 1105, as shown in FIG. 11A. In another embodiment, the transecting member 1110 may comprise one or more retractable blades configured to pass through the open space 1107 of the dissecting member 1105, as shown in FIG. 11B.

In an embodiment, a device for remote endarterectomy includes an elongated member, having a proximal end, a distal end, and a longitudinal axis therebetween; an endarterectomy unit at the distal end of the elongated member formed by a first member engaged to a second member in a substantial secure alignment with the second member, wherein the endarterectomy unit has a circumferential enclosure configured to separate a plaque core from a blood vessel and an open region surrounded by the enclosure and configured to receive the separated plaque core therethrough; and an actuator coupled to the proximal end of the elongated member for translating the first member relative to the second member across the open space to transect the plaque core received in the open space.

In an embodiment, a method for remote endarterectomy of an occluded blood vessel includes placing an endarterectomy unit engaging a distal end of an elongated member into the occluded vessel, wherein the endarterectomy unit comprises a first member and a second member slidable with respect to one another; directing an exposed end of the plaque core into an open space of the endarterectomy unit defined by a circumferential enclosure; advancing the endarterectomy unit through the occluded blood vessel to dissect a length of the plaque core from the wall of the occluded blood vessel by the enclosure; maintaining the first member and the second member in substantial secure alignment with one another throughout the dissection of the plaque core; remotely severing the length of the plaque core by causing the first member and the second member to slide relative to one another across the open space of the endarterectomy unit to sever the plaque core; and removing the severed plaque core and the endarterectomy unit from the vessel.

In an embodiment, a kit for remote endarterectomy includes an endarterectomy unit disposed at a distal tip of an elongated member, wherein the endarterectomy unit is formed by a first member engaging a second member in a substantial secure alignment with the second member; and wherein the endarterectomy unit has a circumferential enclosure configured to separate the plaque core from the blood vessel and an open region surrounded by the enclosure and configured to receive the separated plaque core therethrough; and an actuator to be releasably attached to a proximal end of the elongated member via a hub for translating the first member and the second member relative to one another across the open space so as to transect the plaque core received in the open space.

All patents, patent applications, and published references cited herein are hereby incorporated by reference in their entirety. It will be appreciated that several of the above-disclosed and other features and functions, or alternatives thereof, may be desirably combined into many other different systems or applications.

What is claimed is:

1. A device for remote endarterectomy comprising:
   an elongated member, having a proximal end, a distal end, and a longitudinal axis therebetween;
   an endarterectomy unit at the distal end of the elongated member formed by a first member engaged to a second member in a substantial secure alignment with the second member,
      wherein the first member and the second member each have a circumferential enclosure configured to together separate a plaque core from a blood vessel and an open region surrounded by the enclosure and configured to receive the separated plaque core therethrough; and
   an actuator coupled to the proximal end of the elongated member for translating the first member across the open region of the second member so as to transect the plaque core received in the open region.

2. The device of claim 1 wherein the first member and the second member each have a flat inner surface to allow the first member and the second member to fit together into the endarterectomy unit.

3. The device of claim 1 wherein the circumferential enclosure has a rounded outer edge and at least one beveled section on an inner edge.

4. The device of claim 1 wherein the first member interlocks with the second member for maintaining the first member and the second member in the substantial secure alignment.

5. The device of claim 1 wherein the first member includes a first cooperating structure on its inner surface and the second member includes a second cooperating structure on its inner surface, wherein the first cooperating structure and the second cooperating structure are joinable together for maintaining the first member and the second member in the substantial secure alignment.

6. The device of claim 1 wherein the elongated member comprises a shaft housing and an actuating tip slidably disposed within the shaft housing, and wherein the first member is disposed at a distal tip of the actuating tip and the second member is disposed at a distal tip of the shaft housing such that the movement of the actuating tip within the shaft housing translates the first member in relation to the second member.

7. The device of claim 6 wherein the actuator comprises:
   a housing; and
   a handle slidably disposed within the housing and coupled to the actuating pin such that movement of the handle within the housing causes the first member to translate relative to the second member.

8. The device of claim 1 further comprising a central a central lumen extending longitudinally along the entire length of the device for navigating the device over a guidewire.

9. The device of claim 1 wherein the actuator comprises:
   a housing; and
   a handle slidably disposed within the housing,
      wherein the handle is operably connected to the first member such that movement of the handle within the housing causes the first member to translate relative to the second member.

10. The device of claim 1 further comprising a hub at the proximal end of the elongated member for detachable coupling of the actuator to the proximal end of the elongated member.

11. The device of claim 1 wherein the first member and the second member are pre-tensioned toward one another to maintain the first member and the second member in the substantial alignment.

12. A kit for remote endarterectomy comprising:
   an endarterectomy unit disposed at a distal tip of an elongated member,
   wherein the endarterectomy unit is formed by a first member engaging a second member in a substantial secure alignment with the second member; and
   wherein the first member and the second member each have a circumferential enclosure configured to together separate a plaque core from a blood vessel and an open region surrounded by the enclosure and configured to receive the separated plaque core therethrough; and
   an actuator to be releasably attached to a proximal end of the elongated member via a hub for translating the first member across the open region of the second member so as to transect the plaque core received in the open region.

13. The kit of claim 12 wherein the actuator comprises:
   a housing; and
   a handle slidably disposed within the housing,
      wherein the handle is operably connected to the first member such that movement of the handle within the housing causes the first member to translate relative to the second member.

14. The kit of claim 12 wherein elongated member comprises a shaft housing and an actuating tip slidably disposed within the shaft housing, and wherein the first member is disposed at a distal tip of the actuating tip and the second member is disposed at a distal tip of the shaft housing such that the movement of the actuating tip within the shaft housing translates the first member in relation to the second member.

15. The kit of claim 12 wherein the first member includes a first cooperating structure on its inner surface and the second member includes a second cooperating structure on its inner surface, wherein the first cooperating structure engages the second cooperating structure to maintain the first and second member in the substantial secure alignment.

16. A device for remote endarterectomy comprising:
an elongated member, having a proximal end, a distal end, and a longitudinal axis therebetween;
an endarterectomy unit at the distal end of the elongated member, the endarterectomy unit formed by a first member and a second member,
wherein the first member and the second member each have a circumferential enclosure configured to together separate a plaque core from a blood vessel and an open region surrounded by the enclosure and configured to receive the separated plaque core therethrough, and
wherein the first member includes a first interlocking structure and the second member includes a second interlocking structure configured to cooperate with the first interlocking structure to maintain the first member in a substantial alignment with the second member when the endarterectomy unit separates the plaque core from the blood vessel; and
an actuator attached to the elongated member, the actuator being configured to move the first member across the open region of the second member to transect the plaque core in the open region of the second member.

17. The device of claim 16 wherein the first interlocking structure includes one or more channels and the second interlocking structure includes one or more posts configured to be slidably inserted into the one or more channels of the first interlocking structure.

18. The device of claim 17 wherein the one or more posts are positioned in a top section of the one or more channels to lock the first member and the second member in alignment when the endarterectomy unit separates the plaque core from the blood vessel.

19. The device of claim 16 wherein the elongated member comprises a shaft housing and an actuating tip slidably disposed within the shaft housing, and wherein the first member is disposed at a distal tip of the actuating tip and the second member is disposed at a distal tip of the shaft housing such that the movement of the actuating tip within the shaft housing moves the first member in relation to the second member.

20. The device of claim 16 wherein the endarterectomy unit includes one or more beveled sections for transecting the plaque core.

* * * * *